United States Patent
Momiyama et al.

(10) Patent No.: US 9,352,992 B2
(45) Date of Patent: May 31, 2016

(54) MICROBIAL FLORA ACTIVATOR AND ITS USE IN TREATING WASTEWATER CONTAINING OIL AND FAT

(71) Applicants: ORIENTNANO CO., LTD., Kanagawa (JP); SCHOOL JUDICIAL PERSON IKUTOKUGAKUEN, Kanagawa (JP)

(72) Inventors: Toshiya Momiyama, Fukushima (JP); Yukihito Konno, Kanagawa (JP); Toshiaki Tsubone, Tokyo (JP)

(73) Assignees: ORIENTNANO CO., LTD., Kanagawa (JP); SCHOOL JUDICIAL PERSON IKUTOKUGAKUEN, Kanagawa (JP)

( * ) Notice: Subject to any disclaimer, the term of this patent is extended or adjusted under 35 U.S.C. 154(b) by 0 days.

(21) Appl. No.: 14/588,056

(22) Filed: Dec. 31, 2014

(65) Prior Publication Data
US 2015/0175458 A1 Jun. 25, 2015

Related U.S. Application Data

(63) Continuation-in-part of application No. PCT/JP2013/070799, filed on Jul. 31, 2013.

(30) Foreign Application Priority Data

Jul. 31, 2012 (JP) ................. 2012-170650

(51) Int. Cl.
C02F 3/34 (2006.01)
C02F 3/12 (2006.01)
B08B 9/027 (2006.01)
C12N 1/38 (2006.01)
C11D 1/835 (2006.01)
C11D 11/00 (2006.01)
(Continued)

(52) U.S. Cl.
CPC ................. *C02F 3/343* (2013.01); *B08B 9/027* (2013.01); *C02F 3/12* (2013.01); *C02F 3/1273* (2013.01); *C11D 1/835* (2013.01); *C11D 11/0041* (2013.01); *C12N 1/38* (2013.01); *C02F 2101/32* (2013.01); *C02F 2103/32* (2013.01); *C02F 2209/001* (2013.01); *C02F 2209/22* (2013.01); *C02F 2303/12* (2013.01); *C02F 2305/04* (2013.01); *C02F 2305/06* (2013.01); *C11D 1/523* (2013.01); *C11D 1/721* (2013.01); *Y02W 10/15* (2015.05)

(58) Field of Classification Search
IPC ........ C02F 3/343,3/1273, 3/12; C11D 11/0041, C11D 1/835; B08B 9/027; C12N 1/38
See application file for complete search history.

(56) References Cited

FOREIGN PATENT DOCUMENTS

| | | |
|---|---|---|
| JP | 9-75976 A | 3/1997 |
| JP | 9-215983 A | 8/1997 |

(Continued)

OTHER PUBLICATIONS

International Preliminary Report on Patentability for Counterpart PCT Appln. No. PCT/JP2013/070799, dated Nov. 12, 2014.

(Continued)

*Primary Examiner* — Chester Barry
(74) *Attorney, Agent, or Firm* — Cherry H. Agris; Agris & von Natzmer, LLP

(57) ABSTRACT

Provided is a microbial flora activator which can prevent the re-bonding of a dispersed oil, fat or the like and can activate microorganisms in an activated sludge treatment system; and a method for treating wastewater containing an oil, a fat or the like using the microbial flora activator.

12 Claims, 23 Drawing Sheets

(51) Int. Cl.
*C02F 101/32* (2006.01)
*C02F 103/32* (2006.01)
*C11D 1/52* (2006.01)
*C11D 1/72* (2006.01)

(56) References Cited

FOREIGN PATENT DOCUMENTS

| JP | 9-38630 A | 10/1997 |
|---|---|---|
| JP | 10-235384 A | 9/1998 |
| JP | 2001-162294 A | 6/2001 |
| JP | 3200314 B | 6/2001 |
| JP | 2001-259673 A | 9/2001 |
| JP | 2003-94062 A | 4/2003 |
| JP | 2003-103286 A | 4/2003 |
| JP | 2004-528852 A | 9/2004 |
| JP | 2006-247566 A | 9/2006 |
| WO | 02094181 A | 11/2002 |

OTHER PUBLICATIONS

International Search Report for Counterpart PCT Appln. No. PCT/JP2013/070799, dated Nov. 12, 2014.

Fig. 8
(A) Before Start of Test (July 20)
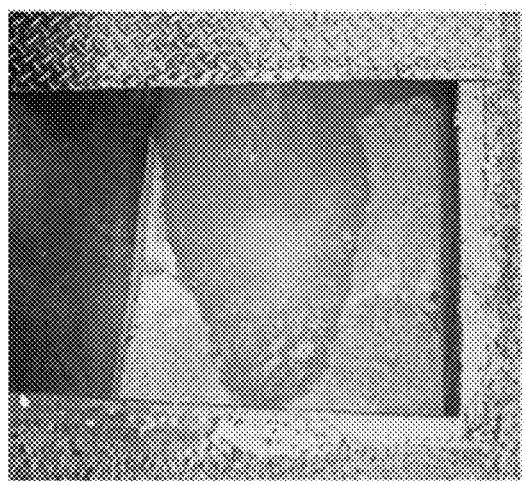
(B) After Start of Test (Aug.10 - Sep.12)
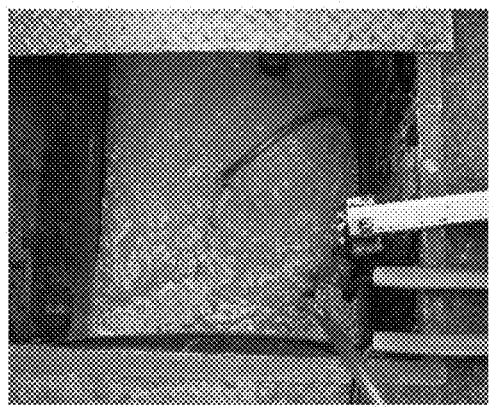
(C) After Start of Test (Oct.11)
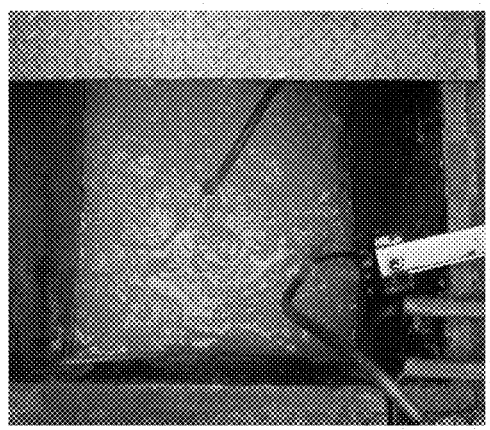

Fig. 9
(A) Before Start of Test (July 20)
(B) After Start of Test (Aug.10 - Sep.12)
(C) After Start of Test (Oct.11)

Fig. 11
(A)
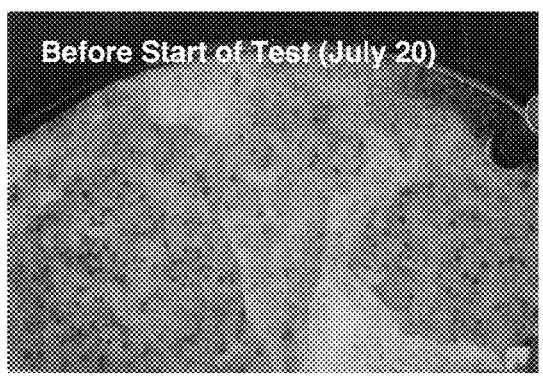
(B)
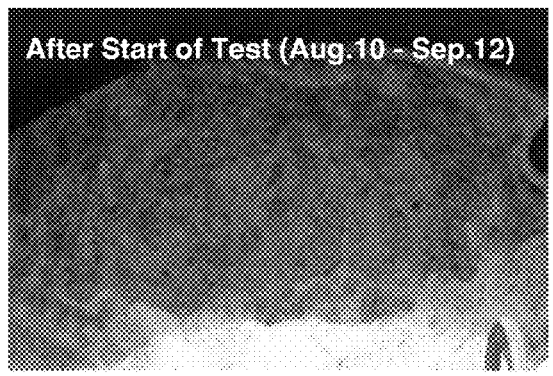
(C)
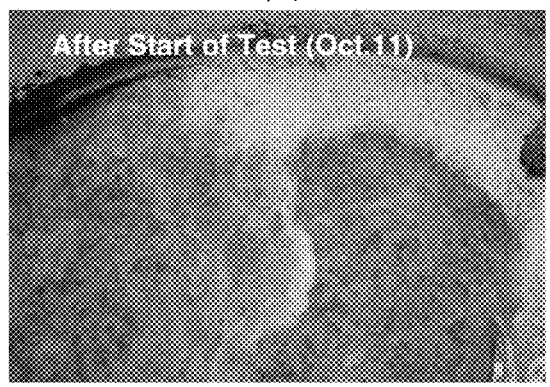
(D) State of Waste Water After Start of Test (Aug.10 – Sep.12)
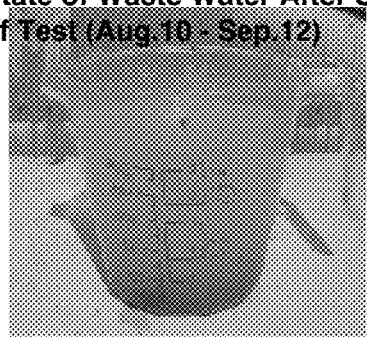
(E)
(F)
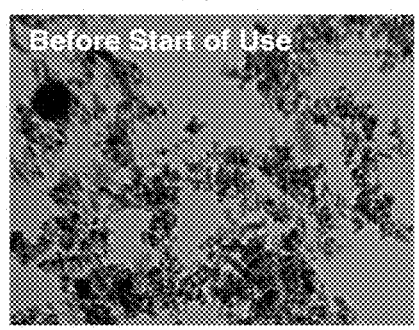
(G)
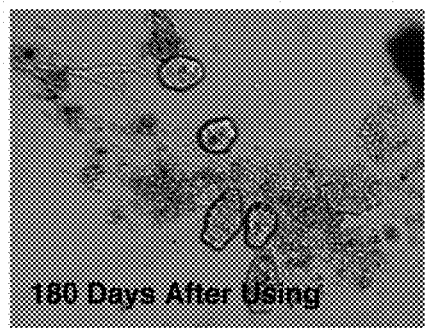

Fig. 12
(A) Near Inlet of Wastewater Pipe Before Use
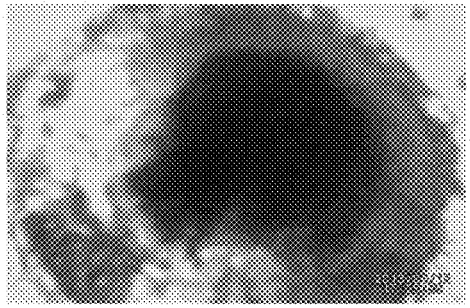
(D) Near Inlet of Wastewater Pipe 1 Month After Use
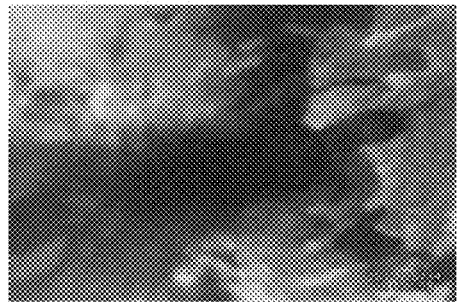
(B) Inside Wastewater Pipe Before Use
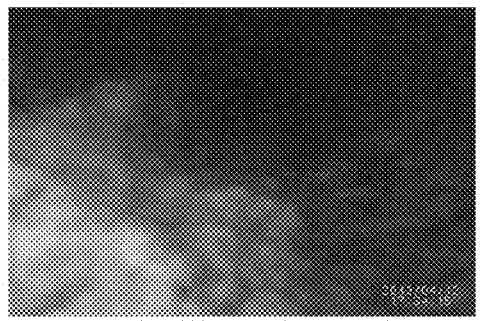
(E) Inside Wastewater Pipe 1 Month After Use
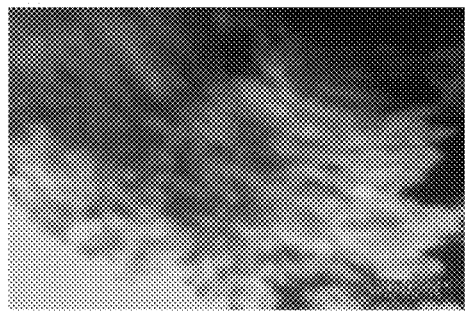
(C) Another Site Inside Wastewater Pipe Before Use
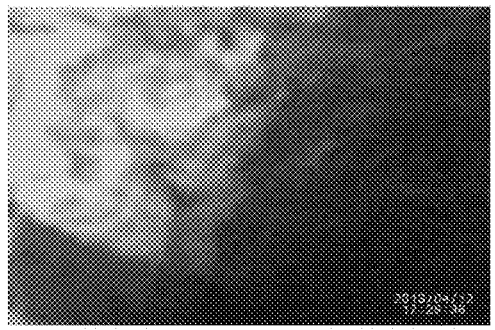
(F) Another Site Inside Wastewater Pipe 1 Month After Use
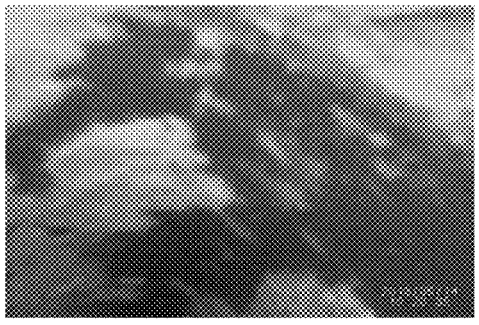

0 = Starting date of Test

Fig. 20
A  Control
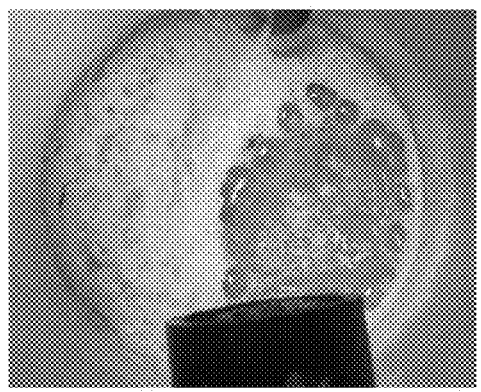
B  Line 2
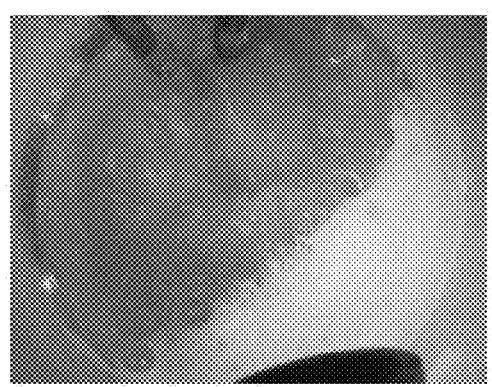
C  Line 3
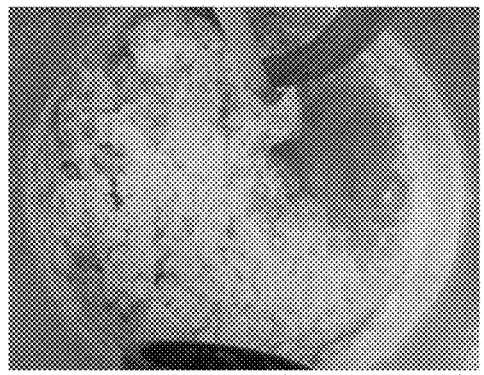
D  Line 4
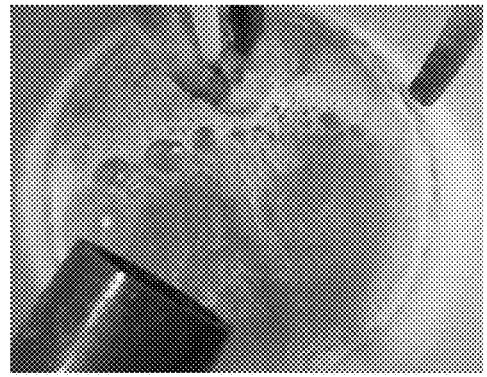

Fig. 23
(A)
(B)
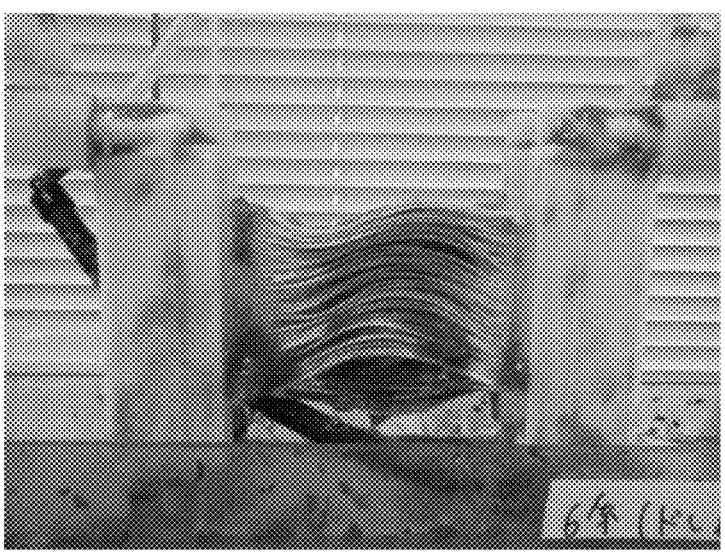

MICROBIAL FLORA ACTIVATOR AND ITS USE IN TREATING WASTEWATER CONTAINING OIL AND FAT

TECHNICAL FIELD

The present invention relates to a microbial flora activator, an anti-microbial agent to the microbes that forms filamentous form comprising said microbial flora activator as an active ingredient, and a method for treating wastewater containing oil, fat, etc. using said microbial flora activator.

BACKGROUND ART

Wastewater which contains an oil, a fat, and a sugar, particularly wastewater and sewage that are discharged from restaurants, kitchens of hotels, and food factories (hereinafter, it is referred to as 'wastewater containing fat and oil and the like'), in the usual case, is treated with an activated sludge through a process as follows.

In the treatment, firstly, an effluent generated while processing food products, and the effluent generated while cleaning are passed through a screen to remove bulky garbage. After that, the effluent is collected in a raw-water tank. Next, the wastewater is put in a regulating tank and is accumulated with aeration. Here, the effluent generated while cleaning also contains a remover or dispersant of fats and oil, such as an existing neutral detergent and an alkaline detergent, mixed therewith.

Thereafter, the effluent that has been accumulated, is transferred to a microbial processing tank while controlling the flow rate with further aeration, and is then subjected to decomposition process by microbes. Moreover, processed water in which, content of oil, fat, and water-soluble organic pollutants has become not more than a regulated value is transferred to a sedimentation tank or a membrane separation tank. Next, after removing insoluble microscopic suspended matter by filtration using a membrane or a difference in specific gravity, the processed water is discharged to outside.

As a technology that adopts such a method of processing, Japanese Patent Application Laid-open Publication No. 2001-235384 (hereinafter, referred to as 'prior art 1'), and Japanese Patent Application Laid-open Publication No. 2001-259673 (hereinafter, referred to as 'prior art 2') have been proposed.

The most typical wastewater treatment method for the decomposition of an organic substance by using aerobic microorganisms is an activated sludge method. After blowing air in the effluent for a long time, the aeration is stopped to allow the effluent to stand and a flocculated brown muddy material is settled out as sedimentation. The brown muddy material is composed of aerobic bacteria and protozoa generated by utilizing organic materials, nitrogen, and phosphorus as a source of nutrition, and appears exactly as if mud is dissolved in water and is called activated sludge. The activated sludge process is a processing method in which, the sludge is added to the effluent, and serially aeration and sedimentation are carried out. Since the activated sludge process has a long history, and is well improved, and has a high efficiency of eliminating organic materials in the effluent, it has been widely used for processing urban drainage, human sewage, and organic industrial wastewater.

In recent years, a wastewater treatment method for separating solid-liquid by using a membrane (hereinafter, it is referred to as 'prior art 2') has also been used.

In a technology according to prior art 1, a microorganism immobilized carrier is formed by random tangling of heat-fusible fibers of polypropylene, and microorganism on the heat-fusible fiber. Prior art 1 is superior from a viewpoint of retaining sufficient amount of microorganism while maintaining a sufficient water flushability, by using the carrier composed of the heat-fusible fibers having a thickness in a range of 50 deniers to 3,000 deniers, and a fiber density in a range of 750 g/m$^3$ to 2,000 g/m$^3$.

However, in a case of processing the above-mentioned fat and oil containing the wastewater, large particles of fat and oil formed in the wastewater are prone to be adhered to the carrier once again, and cause blockage. Therefore, the particles of oil and fat should be in a state without cohering, by dispersing the oil and fat to a certain extent, and making a particle-diameter uniform. If not, the decomposition efficiency by the microorganism that is fixed to the carrier is not improved.

Moreover, the technology according to prior art 2 is superior that a capacity of oil processing is improved significantly from the following viewpoints: at least 80% of volume of an emulsified oil is adjusted to have the particle diameter in a range of 1 μm to 100 μm, and even in the wastewater with comparatively higher oil concentration of 200 mg/l or more, the oil concentration in the water treated in the wastewater treatment equipment becomes low.

When the wastewater containing high concentrations of oil and fat is processed, addition of the above-mentioned dispersant of oil and fat to the raw water tank makes the oil and fat in the effluent disperse once. However, particles of dispersed oil and fat form lumps of a large particle diameter, and are adhered to accumulate on an inner wall of the wastewater channel in the following process. Namely, once dispersed particles of oil and fat are recombined to gradually become large particles. Then, the wastewater is separated to an aqueous phase and an oil phase.

During the process of recombining, the lump is formed by incorporating suspended solids (hereinafter, called as 'SS') in the water. The suspended organic or inorganic substances can be separated by filtration or centrifugation. Such lumps not only require a long time for microbial decomposition but also adhered and accumulated on the inner wall of the wastewater channel.

Therefore, the lumps, which have formed as a result of adding the dispersant of oil and fat to the raw water tank adhere to both of the inner walls of the raw water tank and pipes that send the raw water to the aeration tank causing blockage of pipes. Particularly, when an alkaline detergent is used, oil and fat in the sewage become solid to combine with solid matter to form scum. When the scum is increased in a floatation equipment and in an oil-water separation tank during the process of the effluent treatment, it turns into a metal soap in the presence of metal ions in water to generate hard deposits such as a rock in the plant. It is difficult to remove such deposits by cleaning.

The technology of the prior art 3 is superior in that the activated sludge is not settled naturally because of bulking, does not flow outward (carry-over) toward processing water, and the concentration of the activated sludge being retained in a reaction tank does not depend on a spontaneous sedimentation property and a size of the final settling tank. Here, the term, "bulking", is a phenomenon in which, an SVI (sludge volume index) rises up to about 300 due to swelling of the activated sludge, thereby it makes difficult spontaneous sedimentation separation. In other words, it means that the swelled activated sludge becomes inseparable from water by natural sedimentation separation, due to the weakened sedimentation property of the activated sludge. Moreover, SVI is an index that indicates consolidation characteristics of the sludge. The inseparable activated sludge in the sedimentation tank that overflows from the tank due to the bulking is referred to as "carry-over". However, when the wastewater contains a large amount of oil content, it is necessary to replace the membrane frequently. Moreover, clogging which occurs without backward washing causes trouble, and it takes time for maintenance of the membrane.

In recent years, a detergent labelled to be capable of refining oil and fat has also been marketed. However, in many cases, an effect on microbial processing in the wastewater treatment facility has not been taken into consideration, because the refined oil and fat particles are recombined in a short time. Moreover, a control method adapting to changes occurring due to flow of the refined oil and fat into the microbial processing equipment has not been established.

Therefore, the sludge (sediments having strong odor including organic substances prone to decomposition generated in the process of sewage treatment, industrial wastewater treatment) deposited with the oil in a path of the wastewater treatment is peeled, and they flow in to the microbial processing tank in a large amount. This is a tough trouble to deal with.

Moreover, there also was a problem that a sufficient processing could not be carried out, because it is unable to cope with fluctuation in dissolved oxygen (hereinafter, called as "DO") and mixed liquor suspended solid (hereinafter, called as "MLSS") derived from a change in biota activity. Since the activated sludge is a sludge containing microorganisms for cleaning, MLSS is used as an index indicating cleaning capability, assuming it to be the amount of microorganisms. Stabilizing the MLSS in an appropriate range forms the basis of water quality management.

By this, there is a strong social need for treating the wastewater containing oil and fat and so forth to carry out a sufficient process for preventing the sludge deposition, coping with a rapid increase of load due to peeling off the deposited sludge, and the fluctuation of the dissolved oxygen. Here, DO denotes oxygen dissolved in water (dissolved oxygen), and that in the pure water at 20° C. under 1 atm is approximately 9 mg/L. A quantity of oxygen consumed is large in highly contaminated water and the dissolved oxygen decreases. Thus, the cleaner the water, the greater the amount of dissolved oxygen. The concentration of the dissolved oxygen decreases with a rise in water temperature, a fall in the atmospheric pressure, and a rise in concentration of salt. When the algae grow remarkably, the carbon assimilation effect becomes increasingly active, which leads to supersaturated dissolved oxygen. If the dissolved oxygen is deficient, it threatens survival of fish and shellfish. Since water becomes anaerobic to generate methane and hydrogen sulfide, it causes a foul smell.

In order to improve the situation of the wastewater treatment, introduction of microbial preparation and aeration with oxygen have been carried out. However, when the lumps including the above-mentioned oil and fat are contained in the wastewater, decomposition of such lumps is slow. Oil and fat utilizing bacteria cannot sufficiently decompose the fat and oil in a practical treatment tank in a regular processing time (about 1 day), because of recombination the dispersed oil and fat etc.

Under such circumstances, in a standard activated sludge treatment system, a malfunction of solid-liquid separation occurs, and the sludge sedimentation becomes worse due to generation of filamentous microbes in which bacteria is connected to form a filament shape. As a result, the increase of the dehydration amounts is required. Moreover, flocculation sedimentation agent is heavily used to increase the scum in the floatation equipment, which leads to increased industrial waste generated in the wastewater treatment. Maintenance and management of the facility thus becomes difficult.

Furthermore, even in a system which uses the activated sludge and membrane, clogging of the membrane is caused by the deteriorated solid-liquid separation, growth of the filamentous microbes, and adhesion of the oil-containing sludge and filamentous microbes to a surface of the membrane. By this, a pressure against a membrane becomes higher. Also, it leads the increase of the activated sludge amount to be extracted to cause the problem for the maintenance becoming more time-consuming.

In a treatment system that uses a carrier, blocking of the carrier due to untreated oil and fat content occurs, which not only prevents the carrier from functioning, but also gives the reduction of a substantial capacity of the processing tank.

As mentioned heretofore, there is a strong social need for a microbial flora activator which prevents re-bonding of dispersed oil and fat, as well as activates the microorganisms in the activated sludge treatment system.

SUMMARY

The inventors of the present invention conducted their devoted studies under the above-mentioned circumstances, and accomplished the present invention.

Namely, the first aspect of the present invention is a microbial flora activator comprising: 0.0005 to 8 wt % of polyoxyalkylene alkylether having a carbon number in a range of 13 to 22, and 0.0005 to 2 wt % of fatty acid dialkanolamide as main components; and water as a remainder. Here, the microbial flora refers to an aggregate of microorganisms contained in the activated sludge used in the activated sludge method.

Moreover, the polyoxyalkylene alkylether preferably has a branched chain, and that the added molar number of ethylene oxide is either between 8 and 10 or between 16 and 20.

Also, the polyoxyalkylene alkylether is preferably a compound selected from the group consisting of polyoxyalkylene tridecylether, polyoxyalkylene tetradecylether, polyoxyalkylene pentadecylether, polyoxyalkylene isocetyldecylether, polyoxyalkylene hexyldecylether, polyoxyalkylene heptyldecylether, polyoxyalkylene octyldecylether, polyoxyalkylene octyldodecylether, polyoxyalkylene nonyldecylether, polyoxyalkylene decyldecylether, polyoxyalkylene undecyldecylether, and polyoxyalkylene behenylether.

Furthermore, the polyoxyalkylene alkylether is preferably the compound selected from the group consisting of polyoxyethylene ethers and polyoxypropylene ethers. Moreover, the fatty acid dialkanolamide is preferably the compound selected from the group consisting of coconut-oil fatty acid diethanolamide and coconut-oil fatty acid dipropanolamide.

The second aspect of the present invention is an anti-filamentous bacteria agent having the above-mentioned microbial flora activator as an active ingredient.

The third aspect of the present invention is a pipe cleaning agent having the above-mentioned microbial flora activator as an active ingredient.

The fourth aspect of the present invention is a method for treating wastewater containing oil and fat and the like comprising the steps of: (a) introducing the microbial flora activator as set forth above to raw water; (b) eliminating dispersed oil and fat in the raw water by using the microbial flora activator along with other organic contaminants to process; and (c) gravity separating the activated sludge stably by improving sedimentation property of activated sludge in an aeration tank without a flocculate coagulator, or separating with a membrane.

Here, in the introducing step, the microbial flora activator and the oil and fat in the raw water are stirred to disperse the oil and fat to refine them. Then the dispersed and refined oil and fat are biodegraded by using aeration with other organic contaminant elements efficiently. Moreover, the sedimentation property of the sludge is improved by the activation of the microbial flora, and a large number of protozoan organisms and multicellular microorganisms are generated, thereby facilitating autolysis of the sludge, and advancing the decomposition process by the microorganism.

Next, in the precipitating activated sludge step, the sedimentation property of the activated sludge is improved, so it can be separated without the flocculation coagulator. Moreover, in the membrane separation step, the activated sludge and wastewater are separated by using the membrane. Furthermore, in dehydration step, excessive sludge is extracted.

In the introduction step, it is preferable to introduce the microbial flora activator to raw water stored in a raw water tank or a raw-water equalizing tank.

Moreover, an amount of the microbial flora activator to be input in the input step is in a range of 0.0003 to 0.02% (v/v) against a volume of the wastewater that flows into the raw water tank or the raw-water equalizing tank. More preferably, the amount of the microbial flora activator is in a range of 0.0005 to 0.01% (v/v). Here, in the process of treating the raw water containing oil and fat and the like, a pressure floatation treatment step is preferably to be provided between the microbial processing step and the activated sludge sedimentation step.

However, in the present invention, the treatment in the microbial processing step proceeds smoothly, because of the oil and fat being refined. Therefore, the wastewater may be sent to the subsequent treatment step without eliminating a large portion of oil content in the pressure floatation treatment step. Accordingly, the SS component is mainly eliminated in the pressure floatation treatment step.

Furthermore, a concentration of dissolved oxygen in the contaminated water in the aeration tank is preferably in the range of 0.1 mg/L to 5 mg/L, and that of the suspended matter (MLSS) is in the range of 4,000 to 10,000 mg/L. More preferably, the concentration of dissolved oxygen is in a range of 0.5 mg/L to 3 mg/L, and that of the suspended matter (MLSS) is in the range of 5,000 to 9,000 mg/L.

In the present invention, a membrane separation unit may be used for the activated sludge separation;this membrane unit preferably contains hollow fibers. According to the present invention, there is provided a microbial flora activator being capable of maintaining the dispersed state including the particle having a certain range of the diameter composed of oil and fat and the like to activate the microbial flora, even when the content of the fat, oil and the like in the wastewater containing oil and fat and the like is high.

Moreover, by using a method for treating the wastewater according to the present invention, which uses the microbial flora activator, the wastewater is efficiently treated in a short time, while suppressing adhesion of deposition to inner walls of a treatment tank, to carrier, and inside of pipes. By this, it is possible to suppress an amount of scum, pressure floatation froth, and excessive sludge generated.

Moreover, by using the diluted microbial flora activator of the present invention as a detergent or a pipe cleaning agent, it is possible to suppress choking of the wastewater pipes and side ditches, and malfunctioning of the wastewater equipment due to oil and fat etc.

BRIEF DESCRIPTION OF THE DRAWINGS

FIG. 8 includes photographs showing the changes for the state of the oil-water separation tank before and after using the microbial flora activator of the present invention. (A) shows the state before the test start (July 20), (B) shows that after the test start (between August 10 to September 12), and (C) shows that after the test start (October 11).

FIG. 9 includes photographs showing changes for the states of the raw-water equalizing tank before and after using the microbial flora activator of the present invention. (A) shows the state of the tank before test start (July 20), (B) shows the state of the tank after the test start (between August 10 to September 12), and (C) shows that after test start (October 11).

FIG. 11 include photographs showing the changes for the state of the second carrier aeration tank before and after using the microbial flora activator of the present invention. (A) shows the state of the tank at the time before the test start (July 20), (B) shows the state of the tank after the test start (between August 10 to September 12), (C) shows the state of the tank after the test start (October 11). (D) shows the state of the wastewater after the test start (between August 10 to September 12). (E) shows the state of the wastewater after the test start (October 11). (F) is a photomicrograph showing the state of the microbial flora before using the microbial flora activator of the present invention, and (G) is a photomicrograph showing the microbial flora 180 days (approximately 6 months) after the start of use.

FIG. 12 includes images of a CCD camera showing the state of oil adhered to the wastewater pipe before and after introducing the microbial flora activator of the present invention. (A) is the image showing the oil adhered state near an inlet of the wastewater pipe before introducing. Each of (B) and (C) shows the oil adhered state inside of the wastewater pipe before introducing, and (D) to (F) are the images showing those of the oil adhered state at the time of 1 month after the use at the same location as mentioned above.

FIG. 20 is a photograph showing the sludge state in each line, with (A) being a control and B, C and D being lines 2,3 and 4 respectively.

FIG. 23 is a photograph showing the state of the membrane unit used as the control and that used in the present example, after the test completion.

DETAILED DESCRIPTION

Figure 1:
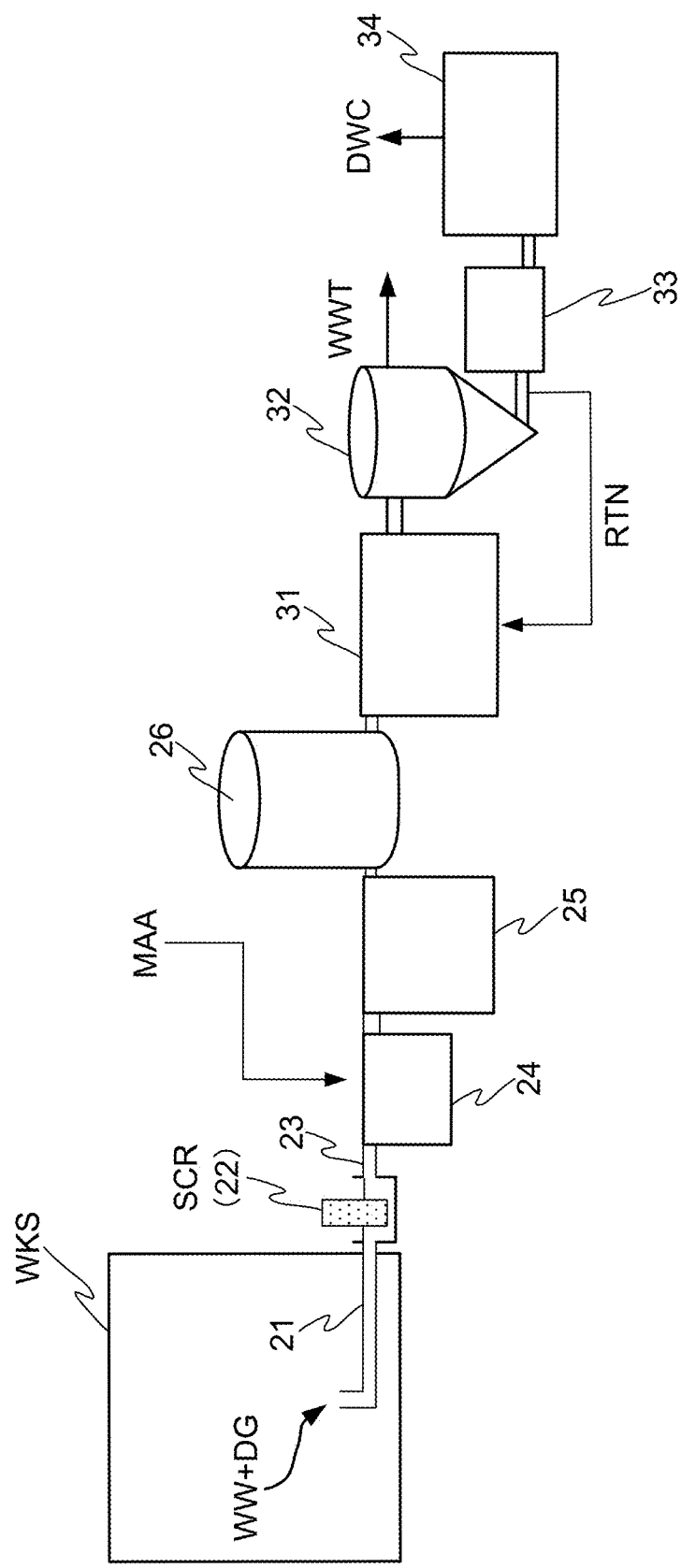
FIG. 1 is a diagram showing an example of a process for treating the wastewater containing oil and fat and so forth.
Figure 2:
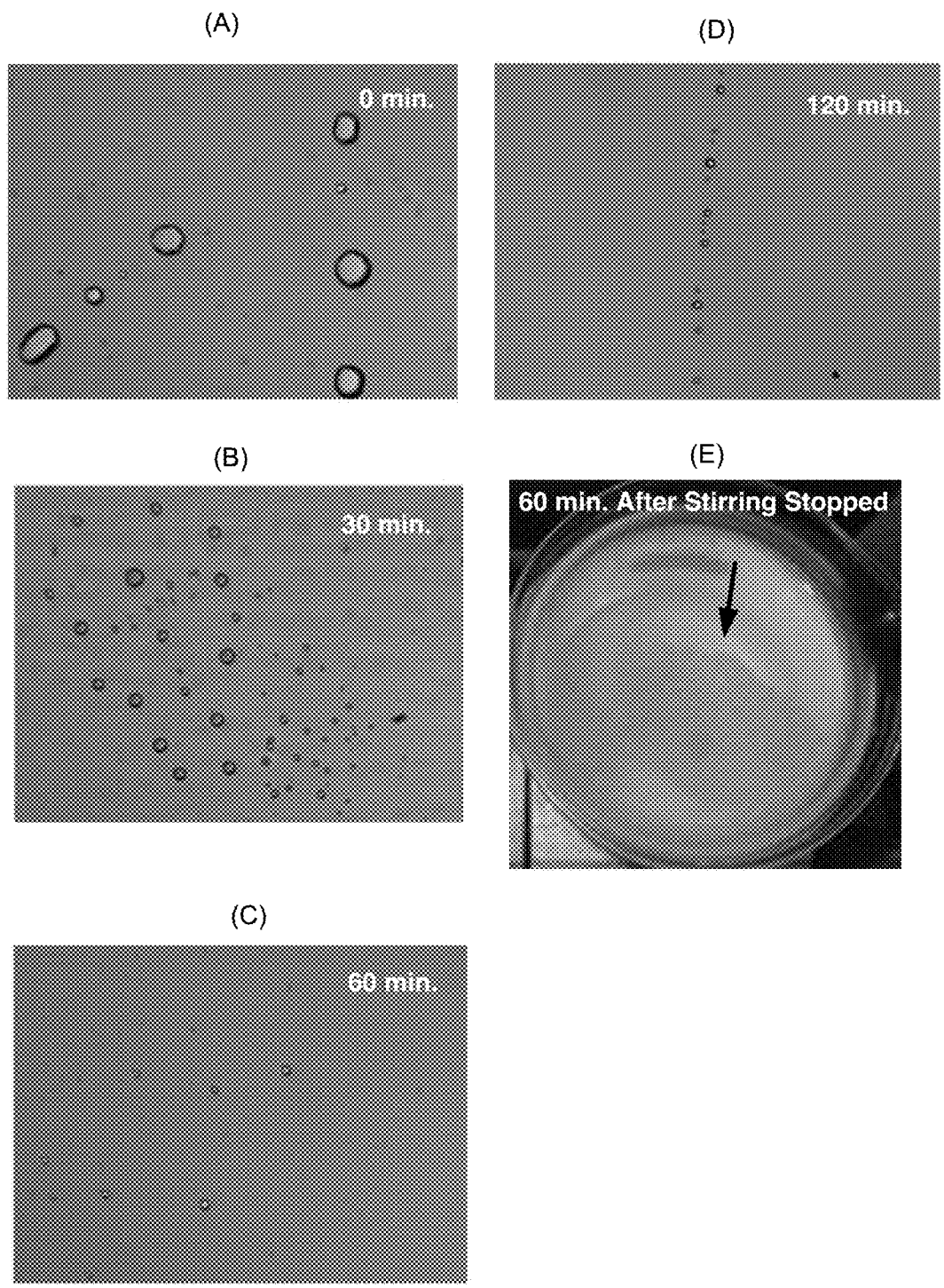
FIG. 2 is a photograph showing time dependent changes of dispersion of oil and fat, when the microbial flora activator of the present invention is added to stir. (A) Shows a state immediately after the stirring is started (0 minutes), (B) to (D) show states after 30 minutes, 60 minutes and 120 minutes respectively from the start stirring, and (E) shows the dispersion state of oil and fat and the like at the time of 60 minutes after the stirring was stopped.
Figure 3:
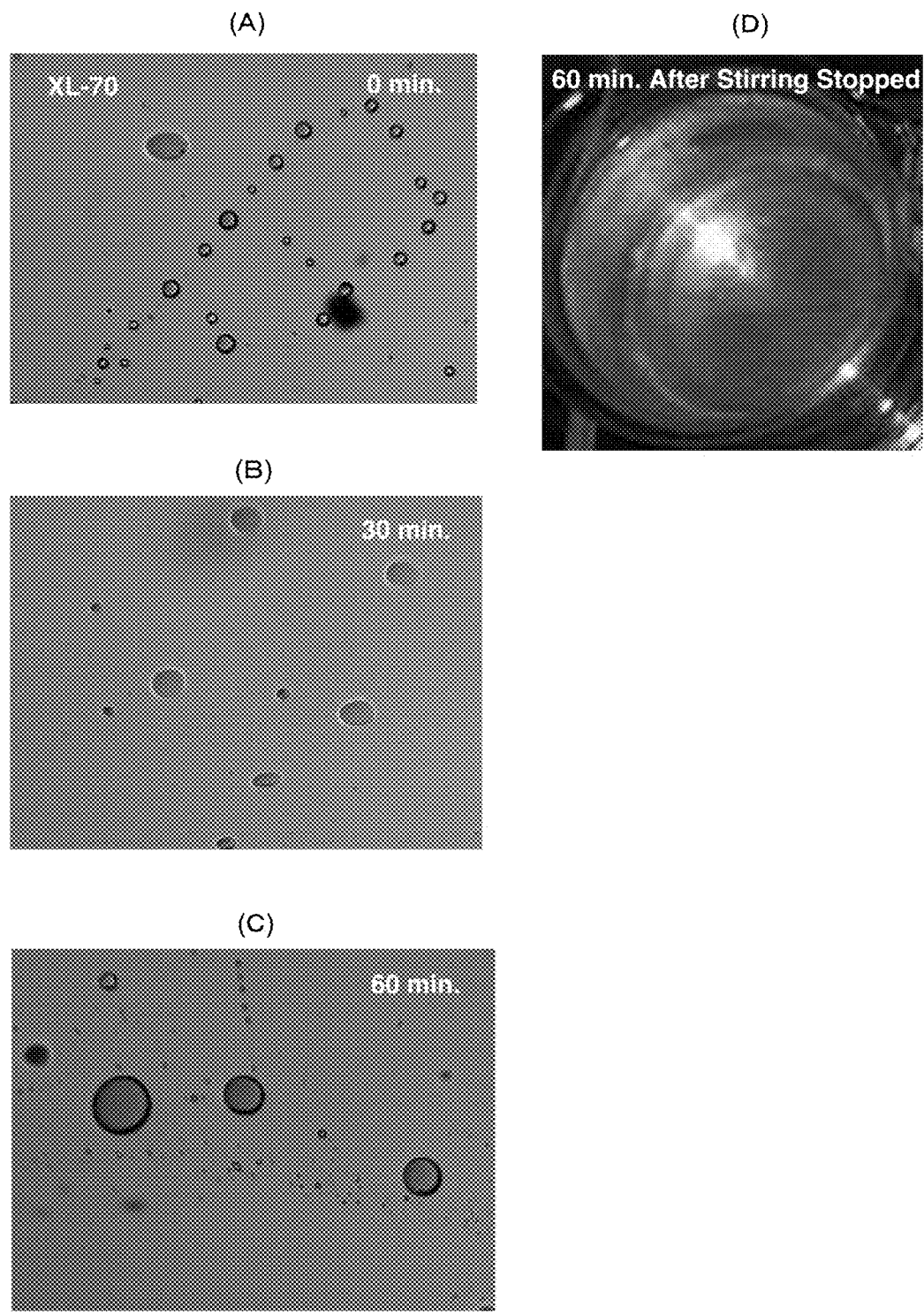
FIG. 3 is a photograph showing the time dependent changes of dispersion of oil and fat, when the XL-70 is added. (A) Shows the state immediately after the stirring is started (0 minutes), (B) and (C) show those after 30 minutes and 60 minutes respectively from the stirring start. (D) shows the dispersion state of oil and fat and the like at the time of 60 minutes after the stirring was stopped.
Figure 4:
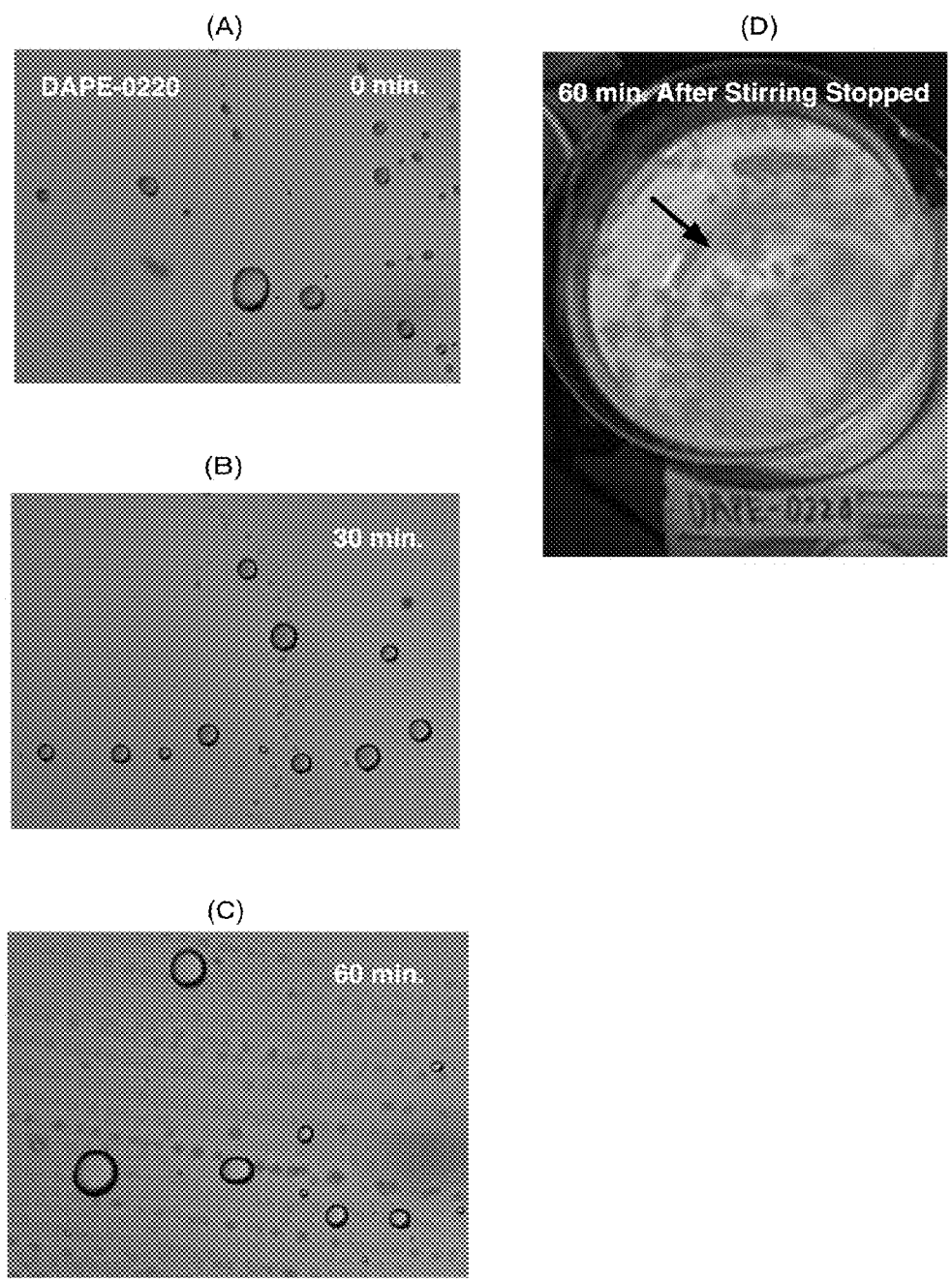
FIG. 4 is a photograph showing the time dependent changes of dispersion of oil and fat, when the DAPE-0220 is added. (A) shows the state immediately after the stirring is started (0 minutes), (B) and (C) show those after 30 minutes and 60 minutes respectively from the stirring start. (D) shows the dispersion state of oil and fat and the like at the time of 60 minutes after the stirring was stopped.
Figure 5:
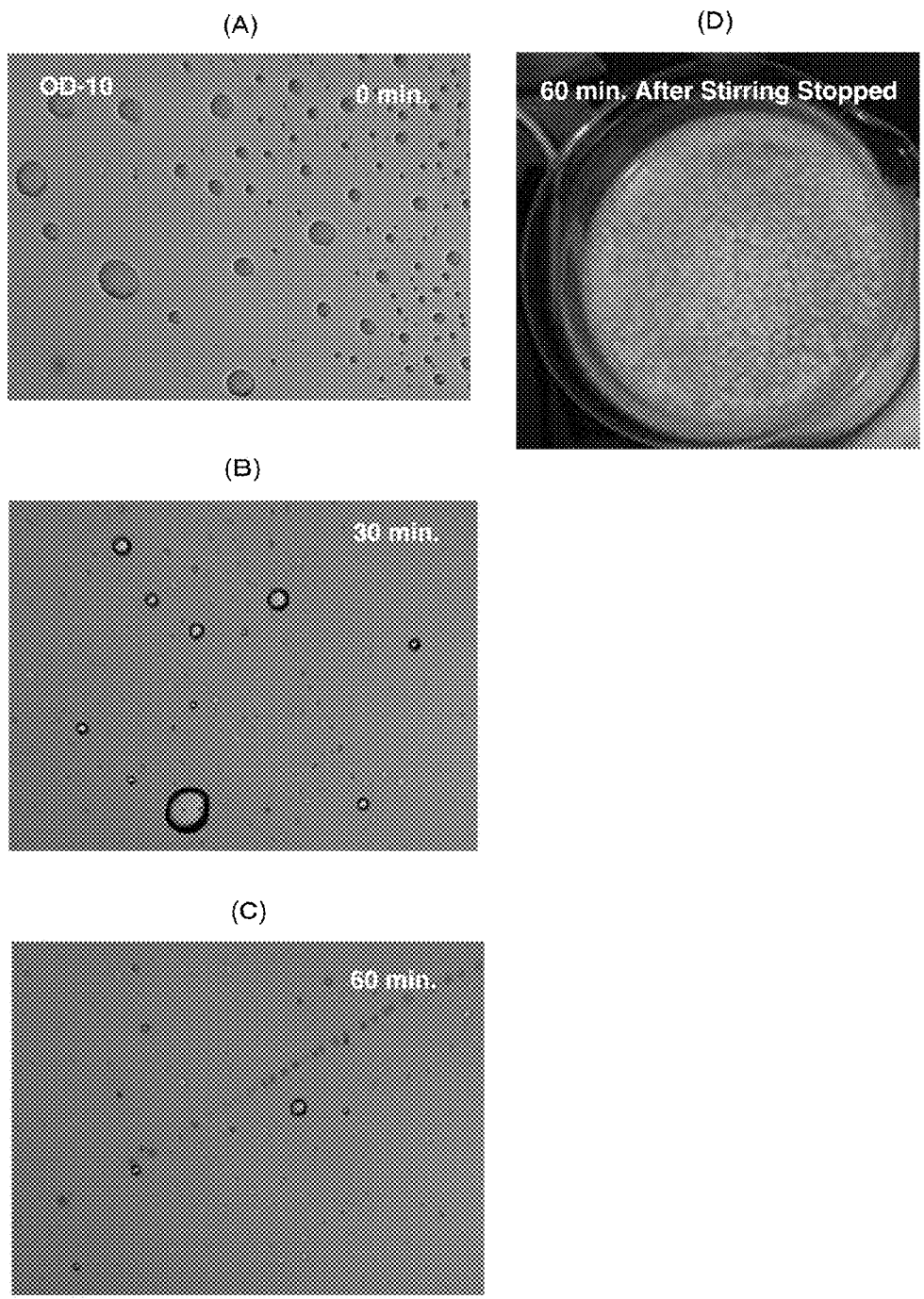
FIG. 5 is a photograph showing the time dependent changes of dispersion of oil and fat, when the OD-10 is added. (A) shows the state immediately after the stirring is started (0 minutes), (B) and (C) show those after 30 minutes and 60 minutes respectively from the stirring start. (D) shows the dispersion state of oil and fat and the like at the time of 60 minutes after the stirring was stopped.
Figure 6:
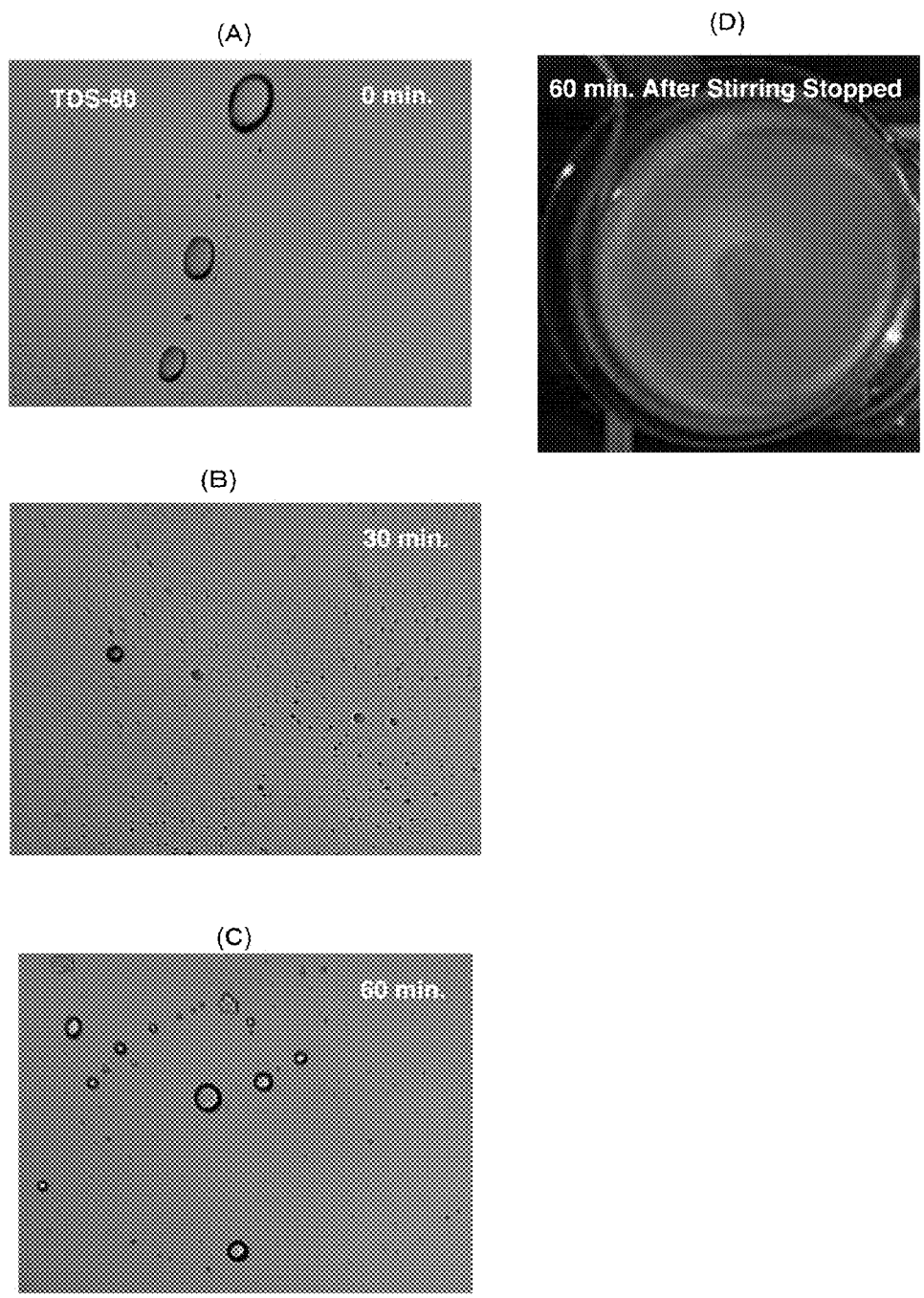
FIG. 6 is a photograph showing the time dependent changes of dispersion of oil and fat, when the TDS-80 is added. (A) shows the state immediately after the stirring is started (0 minutes), (B) and (C) show those after 30 minutes and 60 minutes respectively from the stirring start. (D) shows the dispersion state of oil and fat and the like at the time of 60 minutes after the stirring was stopped.

The present invention will be described below in further detail. A microbial flora activator of the present invention contains 0.1 to 8 wt % of polyoxyalkylene alkylether having the carbon number in the range of 13 to 22 and 0.0005 to 8 wt % of coconut-oil fatty acid dialkanolamide as the main components, and water as a remainder. Here, the polyoxyalkylene alkylether preferably has the branched chain, and the added mole number of ethylene oxide is either between 8 and 10, or between 16 and 20, because this enables the dispersal of oil and fat particles in the wastewater containing oil and fat and the like so as to be a predetermined size, and to maintain them in that state for a predetermined time.

Here, the predetermined particle size refers to those having the diameter between 0.001 to 100 μm, and the predetermined time refers to time from 12 hours to 24 hours.

The polyoxyalkylene alkylether preferably has a branched-chain. Moreover, the polyoxyalkylene alkylether is preferably a compound selected from the group consisting of polyoxyalkylene tridecylether, polyoxyalkylene tetradecylether, polyoxyalkylene pentadecylether, polyoxyalkylene isocetylether, polyoxyalkylene hexyldecylether, polyoxyalkylene heptyldecylether, polyoxyalkylene octyldecylether, polyoxyalkylene octyldodecylether, polyoxyalkylene nonyldecylether, polyoxyalkylene decyldecylether, polyoxyalkylene undecyldecylether, and polyoxyalkylene behenylether, because this enables to disperse oil and fat particles in the wastewater containing oil and fat and the like so as to be a predetermined size, and to maintain them in that state for a long time, as well as it improves the decomposition efficiency of the fat and oil particles.

More preferably, the polyoxyalkylene alkylether is the compound selected from a group consisting of polyoxyethylene ethers and polyoxypropylene ethers, because it further activates the microbial flora to increase the decomposition efficiency of oil and fat and the like. Here, the predetermined size and the time are as mentioned above.

Moreover, more preferably, the coconut-oil fatty acid dialkanolamide is the compound selected from the group consisting of coconut-oil fatty acid diethanolamide and coconut-oil fatty acid dipropanolamide, from a viewpoint of activation of the microbial flora.

The microbial flora activator of the present invention may be prepared by mixing water, 0.0005 to 8 wt % (v/v) of polyoxyalkylene alkylether having a carbon number in the range of 13 to 22, and 0.0005 to 2 wt % (v/v) of fatty acid dialkanolamide.

Concretely, it may be prepared by mixing water, at least one of the 0.0005 to 8 wt % of polyoxyethylene ether and polyoxypropylene ether, and at least one of 0.0005 to 8 wt % of coconut-oil fatty acid diethanolamide and coconut-oil fatty acid dipropanolamide.

Commercially available products may be used as these compounds and products, for example, there are mentioned such as TDX-80D and TDX-100D manufactured by Daiichi Kogyo Co., Ltd., EG-2025G manufactured by Kao Corporation, and 1615, 1620, 2420, OD16, OD20, and BHA-20 manufactured by Nihon Emulsion Co., Ltd.

By using the composition as mentioned above, the microbial flora activator of the present invention, MAA, makes the size of oil and fat particles in the wastewater containing oil and fat (hereinafter, it is sometimes referred to as "raw water"), flowed into a raw water tank 24 or a raw water equalizing tank 25 shown in FIG. 1, so as to be easily decomposed by the microorganisms in the microbial flora, when it is added at the concentration of 0.0003 to 0.02% (v/v) into the raw water. This enables for the microorganism to decompose efficiently the oil and fat particles in the raw water. Moreover, more preferably, the added amount of the microbial flora activator of the present invention is in the range of 0.0005 to 0.01% (v/v). Here, in the process of treating the wastewater containing oil and fat and the like, pressure floatation treatment step may be provided between the microbial processing step and the activated sludge sedimentation step.

Moreover, it is also possible to mix the microbial floral activator of the present invention with a neutral detergent to use the mixture for cleaning containers used for processing of food products in the food factory WKS etc. When the wastewater containing oil and fat and the like washed away by the neutral detergent containing the microbial flora activator has flowed in the raw water tank 24 (hereinafter, it is sometimes referred to as "raw water pit") or the raw water equalizing tank 25 through wastewater pipes 21 and 23, the microbial flora is activated even without adding the microbial flora activator one more time.

In one instance, a wastewater treatment process by using the method described above is shown in FIG. 1. The process includes, (a) the wastewater tank 24 or the wastewater equalizing tank 25 (hereinafter, it is referred to as "equalizing tank 25" in some cases), (b) a floatation equipment 26, and (c) an aeration tank 31. When the amount of wastewater to be treated is large; it is preferable to provide the raw water tank 24 and the raw water equalizing tank 25 separately. These tanks are equipped with a stirrer, and moreover, are preferably equipped with an aeration apparatus. The wastewater containing oil and fat and the like discharged from the factory is generally stored in these tanks for about 1 day.

The microbial flora activator of the present invention is introduced to the raw water tank 24 or the raw water equalizing tank 25 to perform a decomposition treatment of oil and fat and the like. In many cases, oil and fat refined in this process is (a) decomposed by microbial flora (bacteria) occurring in the raw water tank 24 or the raw water equalizing tank 25, and 50% to 90% of the oil and fat contained in untreated contaminated water including contaminant are decomposed and removed, when they are passed through the raw water equalizing tank 25. (b) In the floatation equipment 26, insoluble fine particles in water contained in the raw water are mainly adsorbed on bubbles generated with pressure to be floated, and are separated to be removed. On the other hand, the refined oil and fat, and other organic materials pass through the floatation equipment 26 without removal. (c) In the aeration tank 31, compressed air is blown with the activated sludge to aerobically decompose the contaminant containing the refined oil and fat. (d1) In sedimentation tank 32, the microorganism (activated sludge) grown in the aeration tank 31 is precipitated. Thereafter, a supernatant obtained in the sedimentation tank 32 is released in a river and the like as treated wastewater.

In the process, a bar screen SCR22 is further provided before the raw water tank 24, and (d2) a sludge storage tank 33 and (d3) a dewatering apparatus 34.

Here, the bar screen SCR22 is installed for removing large sized suspended matters in the wastewater from the factory, thereby to prevent choking of pipes caused by the suspended matters, and to prevent heavy load caused by them in the biotreatment step. Moreover, (d2) in the sludge storage tank 33, the activated sludge precipitated and condensed in the sedimentation tank 32 is extracted, and stored while aerating. In the sludge storage tank 33, generally the aeration and storage is carried out for approximately 12 hours to 24 hours.

Then, (d3) by using the dewatering apparatus 34, the water content amount in the activated sludge is reduced from about 98%, which is the water content at extraction, to about 85%.

The activated sludge with the reduced water content is reused, when it may be reused, and it is disposed of as a waste material, if not.

Generally, when a volume of a liquid in the raw water tank 24 or the raw water equalizing tank 25 is given as 650 m$^3$, the amount of the activated sludge extracted per day is about 15 to 25% (v/v) of the volume.

The wastewater containing oil and fat and the like from the factory WKS is treated as follows in the above-mentioned process.

Firstly, in the agent introducing step, the microbial flora activator is introduced to either the raw water tank 24 or the raw water equalizing tank 25. The wastewater in the tank is aerated and stirred for about 12 to 48 hours to obtain primary treated wastewater. It is more preferable to aerate and stir the wastewater for about 24 to 40 hours. When the raw water tank 24 and the raw water equalizing tank 25 are provided separately, the wastewater is aerated and stirred continuously for about 12 to 48 hours at least in the raw water equalizing tank 25. In the event that the stirring time is not more than 12 hours, the dispersion of oil and fat and the like in the wastewater is insufficient, and if it is not less than 48 hours, there is a rise in cost without any further improvement in the effect.

If the stirring time is not less than 24 hours, not only is there a refining and dispersion effect, but the microbial decomposition due to bacteria in the tanks advances. By this, a remarkable load reduction effect is given in the subsequent step, and it is noticeably effective for stabilizing an operation of the treatment facility and reducing the generation of the waste material amount.

When oil, fat, and sludge and the like are already deposited on the inner walls of the raw water tank 24 or the raw water equalizing tank 25, peeling of such deposited oil, fat, and sludge occurs, and lumps of oil, fat, and sludge are also dispersed similarly. As the vanish, the load in the subsequent step increases. Therefore, the operation is adjusted so as to compensate it in the treatment of the subsequent step to adjust the load.

Next, a persistent component in the microbial processing is preliminarily removed from the primary treatment wastewater to obtain secondary treatment wastewater. The removal may be performed in the floatation equipment 26. Concretely, the flocculant is added into the primary treatment to flocculate the water-insoluble persistent fine particles to be adsorbed on the surface of the fine air bubbles generated with a certain pressure to be removed.

In a conventional method, oil and fat are not refined sufficiently at the time point for passing through the equalizing tank 25. Thus, if such wastewater (the raw water) is mixed with the secondary treatment wastewater, the biotreatment for the wastewater is hindered heavily. In order to prevent this, it is necessary for reacting the persistent component such as of oil, fat, and SS with the flocculant to take them in the flock.

In contrast, oil and fat in the waste water are refined sufficiently in the equalizing tank 25 in the present invention to allow it to flow into the secondary treatment wastewater as is. Therefore, it is not necessary to take in oil and fat, which were one of the persistent components heretofore, in the flock. Therefore, it is possible either to reduce a used amount of the flocculant, or without use of it, thereby the amount of froth generated is reduced drastically.

Moreover, as mentioned above, as oil and fat and so forth are dispersed in the equalizing tank 25, and the wastewater load is already reduced. Therefore, when oil and fat passed through the floatation equipment 26, oil and fat and the like concentrations in the primary treatment wastewater is drastically decreased compared to those in the raw water. Also, oil and fat in it are refined. By this, no excessive load is exerted in the microbial processing performed in the subsequent steps.

As described above, when oil and fat and the like are sometimes adhered to be deposited in the facility, a part thereof has already decomposed at the time point in which the present agent is started to be used. In this case, the oil and fat content amount in the wastewater is sometimes drastically increased at the time point that the wastewater is passing through the equalizing tank in transient, and it sometimes increases MLSS. In such case, during a time period till the amount decreases to some extent, the rise in interface level in the sedimentation tank accompanied by the increase of MLSS may be suppressed by adding a commercially available flocculant to the aeration tank or the sedimentation tank. In order to avoid the risk involved in operating the wastewater treatment equipment, to reduce a cost required for the treatments of the flocculant and froth, and to reduce the cost for the operation of the wastewater treatment equipment, it is preferable to gradually reduce the introduced amount of the flocculant, and finally no use, after the content amount of oil and fat in the wastewater is decreased.

The primary treatment wastewater is introduced to the aeration tank 31 containing the activated sludge. In the aeration tank 31, contaminants such as oil and fat are decomposed aerobically by the microbes in the activated sludge. In other words, the aeration tank 31 plays the most important role in the treatment process.

For efficient decomposition treatment on the contaminants in the wastewater, the capacity of the aeration tank 31 is important. The capacity is generally calculated by using BOD volume load. Here, the BOD volume load is expressed by an amount of BOD in kilograms per day per 1 $m^3$ volume of the aeration tank 31. BOD stands for biochemical oxygen demand (Biochemical Oxygen Demand), and refers to the amount of oxygen (generally, mg/L is used) consumed when an organic material in water is biochemically oxidized or decomposed in presence of dissolved oxygen. As the value of BOD becomes higher, it implies that the water is contaminated. In a typical wastewater treatment facility, it is operated at the BOD volume load of about 0.4 kg/$m^3$/day in many cases. A larger BOD volume load requires higher treatment capacity. However, since this leads to a decreased stabilization of fluctuation in the load, it becomes necessary to pay attention to its control and maintenance. In contrast, when the microbial flora activator of the present invention is used, it is possible to carry out the treatment stably even for the BOD volume loads surpassing 1 kg/$m^3$/day.

Here, SS is obtained by measuring a weight of a filter paper, which filtered a certain amount of water. A higher value (mg/L) measured implies higher water turbidity.

For reducing the BOD, it is important to determine the extent the microbes exist in the aeration. As the index of it, MLSS (Mixed Liquor Suspended Solids) concentration (mg/L) is used. In other words, MLSS refers to the activated sludge floating in the wastewater inside the aeration tank, and to be precise, includes components other than the microorganism, such as inorganic suspended solids. However, in a general wastewater treatment, it is used as the index for the activated sludge concentration. MLSS concentration is generally set in a range of approximately 3,000 to 6,000 mg/L, but in the method of the present invention, it is possible to set the MLSS concentration in a range of approximately 4,000 to 10,000 mg/L. If MLSS becomes less than 4,000 mg/L or 10,000 mg/L or more, the sedimentation property of the activated sludge is degraded due to carry-over described later to cause the problem that supernatant water cannot be obtained.

In the method for treating the wastewater containing oil and fat and the like of the present invention, the MLSS concentration may be increased up to approximately 10,000 mg/L at the most, provided that an aerobic environment in the aeration tank 31 is maintained, and there is no risk of carry-over. It is preferable to be maintained at a higher value because of the wastewater treatment efficiency. However, since it increases the necessary aeration amount, the cost required for the entire of the treatment and for this should be balanced.

When an activated sludge method is used, in order to improve the quality of the treatment water treated in a cleaning tank, it becomes important to perform effective solid-liquid separation of the treatment water and microorganism, which utilizes the organic materials in the raw water flown into the tank to grow, in the sedimentation tank. However, when filamentous microorganisms such as filamentous microbes are seriously increased to swell the activated sludge and the SVI (sludge volume index) expresses consolidation of the sludge, it does so up to about 300. It leads to the deterioration of the sedimentation property of the activated sludge, and they are hardly spontaneously precipitated. Such a phenomenon is referred to as "bulking".

When bulking occurs in a sewage plant, the activated sludgefails to be separated from the liquid in the sedimentation tank, and overflows. This phenomenon is referred to as "carry-over".

Bulking may be due to an abnormal growth of the filamentous bacteria and other than it. In a typical bulking, abnormally grown filamentous bacteria entangle even in the sedimentation tank to prevent their precipitation; thereby the supernatant cannot be obtained. Other reasons for bulking may be the formation of dispersed state bacteria, which should be originally aggregated because of excess aeration amount; the blocked mutual aggregation among the bacteria because of the production of highly viscous secretions, and the insufficient sedimentation by the buoyance derived from the flocks of the active sludge to which oil and fat and the like insufficiently biodegradated are adsorbed.

When the bulking as described above occurs, the sludge amount returned to the aeration tank 31 becomes insufficient, thereby decreasing the activated sludge concentration in the aeration tank to also decrease the treatment efficiency. Not only this, when more water is removed from sludge than necessary, it requires the treatment of the excess sludge and use of much flocculation sedimentation agent, resulting in high cost.

Here, the activated sludge is set aside for certain time, and the sludge amount precipitated expressed in percentage is referred to as SV (sludge volume). Moreover, the index expressing the sedimentation of the activated sludge is referred to as SVI (sludge volume index), and indicates a volume (mL) occupied by 1 g of the sludge when the activated sludge is kept stationary for 30 minutes.

$$SVI = SV \times 10000 / MLSS$$

SVI=100 implies that 1 g of the activated sludge occupies a volume of 100 mL. In a normal aeration tank, it is appropriate in the range of 50 to 150, and when the value is 200 or higher, it is said to be in the bulking state.

In the method for treating water of the present invention, DO is regulated in the range of 0.1 mg/L to 4 mg/L, and while observing the value and the amount of the activated sludge to be dehydrated, MLSS is adjusted in the range of approximately 4,000 to 10,000 mg/L.

As mentioned above, when an operation control of the wastewater treatment is carried out by using the method for treating wastewater containing oil and fat of the present invention, a large number of protozoa and multicellular microorganisms are generated in the sludge, and a speed of increase in the activated sludge drops due to endogenous respiration. Therefore, it is possible to maintain the required amount of water to be released while dehydrating the amount of excessive water removed from the sludge.

Examples of the present invention are described below. However, the present invention is not restricted to the examples described below. Moreover, percentage in the examples, unless otherwise noted, is weight-based (mass-based).

EXAMPLES

The present invention is not restricted in any way to the description of the embodiment and examples of the invention. Various modified embodiments that readily occur to a person skilled in the art, without departing from the scope of the invention claimed, are included in the invention. The present invention will be described below in further detail by using the examples.

Example 1

Investigation of composition of microbial flora activator

Components can be used as a microbial flora activator was studied. Compositions shown in the following Tables 1 and 2 were prepared by mixing 0.056% polyoxyalkylene alkylether or polyoxyalkylene with water, and a diameter of dispersed particles of oil and fat and properties such as an affinity for flocking, re-bonding (recombining) property, dispersion rate were studied. Results are shown in the Tables 1 and 2.

In Table 1 and Table 2, *1 to *5 are as follows.

1: polyoxypropylene alkylene-ether
2: POATED: polyoxyalkylene tridecylether
OcDd: polyoxyalkylene octyldodecylether
IsSe: polyoxyalkylene isocetylether
DeTd: polyoxyalkylene decyltetradecylether
TrDe: polyoxyalkylene tridecylether
Ol: polyoxyalkylene oleylether
Bh: polyoxyalkylene behenylether
Ar: polyoxyalkylene alkylether
OA: polyoxyalkylene oxyalkylene-ether
POAD: polyoxyalkylene decylether
POPDE: polyoxypropylene decylether 3: PRTR (Pollutant Release and Transfer Register: Chemical material discharged and transferred volumes filing system): An undertaker has to keep a track of an amount discharged to the environment, and an amount transferred outside an establishment as waste material and sewage, and report to an administrative agency once a year.

4: PO=propylene oxide
5: possibility of re-bonding in time course.

TABLE 1

| | Examples of present invention | | | | | | | | |
|---|---|---|---|---|---|---|---|---|---|
| | 1 | 2 | 3 | 4 | 5 | 6 | 7 | 8 | 9 |
| Type of activator | | | | | POE.[1] | | | | |
| Manufacturer | Daiichi Kogyo Seiyaku | | Nihon Emulsion | | Kao | | Nihon Emulsion | | |
| Product name | TDX-80D | TDX-100D | 1620 | 520 | EG-2025G | OD16 | OD20 | BHA-20 | 2420 |
| License name specific to type.[2] | POATED | | IsSe | Ol | OcDd | OcDd | OcDd | Bh | DeTd |
| Carbon number of alkyl group (Cn) | 13.[3] | 13.[3] | 16 | 18 | 20 | 20 | 20 | 22 | 24 |
| (EO)n | OA.[3]; Approx. 8 | OA.[3]; Approx. 10 | 20 | 20 | 25 | 16 | 20 | 20 | 20 |
| (EO)n/Cn | 0.61 | 1.3 | 0.80 | 0.90 | 0.80 | 1.25 | 1.00 | 1.10 | 1.20 |
| Presence of branched-chain | Unknown | Unknown | Present | Straight chain | Present | Present | Present | Straight chain | Present |
| HLB | 131 | — | 14 | 13 | 15.7 | 12 | 13 | 13 | 12 |
| Dispersed particle size distribution | Uniform | Uniform | Uniform | Uniform | Uniform | Uniform | Uniform | Uniform | |
| Oil-droplet particle size | Fine | Fine | Fine | Fine | Fine | Fine | Fine | Fine | Coarse |
| Re-bonding (floated oil) | No | Yes (long time) | No | No | No | No | No | No | Bonding |
| Dispersion rate | Low | High | Somewhat low | Somewhat low | Favorable | Favorable | Favorable | Favorable | Somewhat low |
| Judgment of dispersibility | Favorable | Favorable | Favorable | Favorable | Favorable | Favorable | Favorable | Favorable | Somewhat poor |
| Affinity for flocking | Favorable | Favorable | Somewhat favorable | Favorable | Favorable | — | Favorable | — | Hard to say |
| Overall judgment | Not fully acceptable | Not fully acceptable | Not fully acceptable | Acceptable | Acceptable | Acceptable | Acceptable | Not fully acceptable | Not fully acceptable |

TABLE 2

| | Examples for comparison | | | | | | | | | | |
|---|---|---|---|---|---|---|---|---|---|---|---|
| | 1 | 2 | 3 | 4 | 5 | 6 | 7 | 8 | 9 | 10 | 11 |
| Type of activator | PO | | | | | POE.[1] | | | | | |
| Manufacturer | Daiichi Kogyo Seiyaku | Nihon Emulsion | | | Daiichi Kogyo Seiyaku | | | Nihon Emulsion | | | |
| Product name | XL-70 | DAPE-0215 | DAPE-0220 | DAPE-0230 | ET-135 | CD10 | HC-40 | HC-50 | HC-60 | 2425 | TDS-80 |
| License name specific to type.[2] | POAD | | POPDE | | Ar | OcDd | POE hydrogenated castor oil | | | DeTd | TrDe |

TABLE 2-continued

| | Examples for comparison | | | | | | | | | | |
|---|---|---|---|---|---|---|---|---|---|---|---|
| | 1 | 2 | 3 | 4 | 5 | 6 | 7 | 8 | 9 | 10 | 11 |
| Carbon number of alkyl group ($C_n$) | 10 | 10 | 10 | 10 | 12~15[3] | 20 | 53 | 53 | 53 | 24 | 13[3] |
| $(EO)_n$ | OA; Approx. 7 | 15 | 20 | 30 | 9 | 10 | 40 | 50 | 60 | 25 | 8 |
| $(EO)_n/C_n$ | — | 0.67 | 0.50 | 0.33 | 1.33~1.66 | 2.00 | 1.33 | 1.06 | 0.88 | 0.96 | 1.62 |
| Additional molecule; mole no. | — | PO[4]; 2 | PO[4]; 2 | PO[4]; 2 | — | — | — | — | — | — | — |
| Branching | Branched | — | — | Straight chain | Unknown | Branched | Branched | Branched | Branched | Branched | Unknown |
| HLB | 13.2 | Unknown | Unknown | 16 | 13.3 | 10 | 12 | 13 | 14 | 13 | 13.3 |
| Dispersed particle size distribution | Non-uniform | Non-uniform | Non-uniform | Non-uniform | Non-uniform | Non-uniform | Non-uniform | Non-uniform | Non-uniform | Uniform | Uniform |
| Oil-droplet particle size | Coarse | Coarse | Coarse | Coarse | Coarse | Coarse | Coarse | Coarse | Coarse | Fine | Fine |
| Re-bonding (floated oil) | Yes | Yes | Yes | Yes | Re-bonding | Bonding | Yes | Yes | Yes | No | Slight re-bonding |
| Dispersion rate | Low | High | High | Low | High | High | Low | Low | Low | Low | High |
| Judgment of dispersibility | Poor | Poor | Poor | Poor | Poor | Poor | Poor | Poor | Poor | Poor | Poor[6] |
| Affinity for flocking | — | — | — | — | Favorable | — | — | — | — | — | Somewhat favorable |
| Overall judgment | Not acceptable | Not acceptable | Not acceptable | Not acceptable | Not acceptable | Not acceptable | Not acceptable | Not acceptable | Not acceptable | Not acceptable | Not acceptable |

From the results, in a case of polyoxyethylene alkylether, compounds having the carbon number ($C_n$) of the alkyl group is in a range of 13 to 24, the added mole number of ethylene oxide ($(EO)_n$) is in a range of 8 to 20, the ethylene oxide number/ carbon number ($(EO)_n/C_n$) is in a range of 0.6 to 1.62, had both namely, favorable dispersibility and flockphile property (the present Examples 1 to 10). Among them, the composition having the $C_n$ in a range of 13 to 22, and the $(EO)_n$ in a range of 16 to 20 demonstrated more favorable dispersibility and flockphile property.

The compounds having carbon number not more than 10 and that not less than 50 had slow dispersion rates, and a large number of such compounds had a poor dispersibility (Comparative Examples 1 to 4, and 7 to 9). Even with carbon number 20, when the $(EO)_n/C_n$ became not less than 2, the dispersion rate was high but the dispersibility became poor (the comparative Example 6). Moreover, when the $(EO)_n$ was less than 8 or was 25 or more than 25, the dispersibility became poor (the comparative Example 1). In the comparative Example 5, polyoxyethylene alkylether, the dispersion rate was high but the dispersibility became poor.

Accordingly, in the following examples, the composition of the Example 7 comprising 0.0005 to 2 wt % of fatty acid alkanolamide of coconut oil was used.

Example 2

Dispersion Test of Oil and Fat (1) Materials and Methods

To 1 L of tap water, 1g of salad oil (manufactured by Nisshin Oillio Group, Ltd.) and 1 mL of the composition of the Example 7 of the present invention was added in a beaker. A stirring bar was dropped into the beaker and stirred at 500 rpm, the salad oil was dispersed and emulsified to prepare. Instead of the composition of the Example 7 of the present invention, XL-70 (manufactured by Daiichi Kogyo Co., Ltd., the comparative Example 1), DAPE-0220 (manufactured by Nihon Emulsion Co., Ltd., the comparative Example 3), OD-10 (manufactured by Nihon Emulsion Co., Ltd., the comparative Example 6), or TD-80 (manufactured by Nihon Emulsion Co., Ltd, the comparative Example 11) were used, and stirred similarly as the sample 1, and control samples 1 to 4 were prepared.

(2) Measurement Items and Method of Measurement

For the sample 1, and the controls 1 to 4, their dispersion states were observed by using the microscope (×100 magnification) at 30 minutes and 60 minutes after the start of stirring, as the 0 minutes immediately after the start of test. For the sample 1, the state at 120 minutes after the start of stirring was also observed by the microscope. The state at 60 minutes after the end of stirring was also observed grossly. Results are shown in diagrams from FIG. 2 to FIG. 6D.

As shown in FIG. 2(A) to (E), in the sample 1, even at 120 minutes after the stirring start, oil with finely dispersed state was maintained. Even 60 minutes after the stirring stop, re-bonding of dispersed oil particles was not observed. The fine particles of oil dispersed in water made the water cloudy, but almost no oil was floating on a surface of water.

As shown in FIG. 3(A) to (E), in the control 1 (XL-70), oil was dispersed to fine particles once, but was re-bonded after stirring for 60 minutes, and the particles with a large diameter were observed (see FIG. 3(C)). Also, 60 minutes after the stirring stop, oil re-bonded, and an oil film was observed on the surface of water. The number of oil particles dispersed in water being extremely small, clarity of water was high (see FIG. 3(D)).

As shown in FIG. 4(A) to 4(D), in the control 2 (DAPE-0220), almost no change was observed in the oil particle size, and it was demonstrated that oil is not refined with DAPE-0220. At 60 minutes after the stirring stopped, oil re-bonded, and aggregated to float on a water surface. The particles of oil dispersed in water being extremely few, the clarity of water was high (see FIG. 4(D)).

As shown in FIG. 5(A) to (5D), in the control 3 (OD-10), it was observed that the dispersion of oil was favorable, and oil was refined substantially. At 60 minutes after the stirring stop, the oil particles aggregated and floated on a water surface.

The oil particles dispersed in water being extremely few, the clarity of water was high (see FIG. 5(D)).

As shown in FIG. 6(A) to (D), in the control 4 (TDS-80), at 30 minutes after the stirring start, it was observed that oil was well dispersed to fine particles. However, at 60 minutes after the stirring stop, the once refined oil re-bonded, and particles with a large diameter were observed. At 60 minutes after the stirring stopped, the oil particles aggregated and floated on a water surface. The oil particles dispersed in water being extremely few, the clarity of water was high (see FIG. 6(D)).

From these observations, it was shown that, in the sample 1, up to 120 minutes after the stirring start, no re-bonding of the once-dispersed oil particles occurred to maintain the dispersed state, which was maintained up to 60 minutes after the stirring stop.

In contrast, it was shown that the re-bonding of the oil particles occurred during stirring, or no bonding of the oil particles occurred during stirring but re-bonded and aggregated as the stirring stop in the control samples 1 to 4.

Example 3

Water Quality Change in Raw Water Equalizing Tank in the Food Factory 1

(1) Measured Samples and Measurement Items

By using a ladle, 4 L of a liquid was dipped up from the raw water equalizing tank during aeration and stirring, before adding the microbial flora activator of the present invention to the tank in the food factory, and at a time point after 20 days from the start of addition of the activator to measure items shown in the following Table 3. An added amount of the microbial flora activator to the raw water equalizing tank against that of the wastewater inflow was 0.001%. A retention time of the sewage water in the raw water equalizing tank was 18 hours. Any floatation equipment was not used.

TABLE 3

| Measurement | Sampling date | |
|---|---|---|
| items | Before addition | 20 days after addition |
| Water temperature (° C.) | 14 | 7.5 |
| pH | 5.1 | 4.5 |
| SS (mg/L) | 770 (100) | 435 (56.5) |
| n-Hex (mg/L) | 66.4 (100) | 7.9 (11.9) |
| BOD-5 (mg/L) | 1520 (100) | 790 (52.0) |
| BOD-20 (mg/L) | 2690 (100) | 1280 (47.6) |

In the Table 3, figures in brackets indicate percentage when a value before addition is 100. Moreover, BOD-5 indicates an oxygen consumption amount when cultured for 5 days at 20° C. BOD-20 indicates that when cultured for 20 days at 20° C. BOD was measured according to JIS K0102 21.

According to JIS K0102 24, n-Hex (normal-hexane extract) was measured. pH was measured by using a glass electrode for pH measurement, according to JIS Z8805. SS was measured according to JIS K0102 14.1. MLSS defined in JIS B9944 was measured similarly as SS.

At 20 days after the addition start, in spite of drastic decreasing in temperature, each of SS, BOD-5, and BOD-20 was reduced to almost half. Furthermore, n-Hex amount was reduced by almost 90%, and it showed that oil and fat were sufficiently removed.

From the above, it was shown that the sewage water was cleaned, the water quality substantially had improved at a stage of the raw water equalizing tank, and an inflow load to the aeration tank in the latter stage was reduced drastically.

Example 4

Change in SS and the Like in Wastewater from the Food Factory 2 in the Raw Water Equalizing Tank Upon adding 0.0015% of the microbial flora activator of the present invention to the wastewater equalizing tank and adjusting, 3 L of the wastewater, which was passed through the pressure floatation equipment without addition of the flocculant, from another food factory, was sampled similarly as in the Example 3. SS, BOD, and n-Hex in the sample were measured as the same as described above. When the experiment was performed, a water level in the raw water equalizing tank was set to be higher than the conventional water level. The retention time of the sewage water in the raw water equalizing tank was set to 12 hours, and DO was adjusted in a range of 1.0 to 2.0 mg/L. Results are shown in the Table 4.

TABLE 4

| | Sampling day | | | | |
|---|---|---|---|---|---|
| Measurement items | Before adding | day 6 | day 12 | day 19 | day 30 |
| SS (mg/L) | 110 (100) | 110 (100) | 170 (154.5) | 220 (200.0) | 110 (100.0) |
| n-Hex (mg/L) | 101 (100) | 93 (92.1) | 54 (53.5) | 21 (20.8) | 27 (26.7) |
| BOD (mg/L) | 428 (100) | 380 (89.8) | 400 (93.5) | 200 (46.7) | 110 (25.7) |

As shown in the Table 4, the SS value once increased and then dropped, but the n-Hex content decreased in a time dependent manner. Also, the BOD decreased time dependently.

Figure 7:
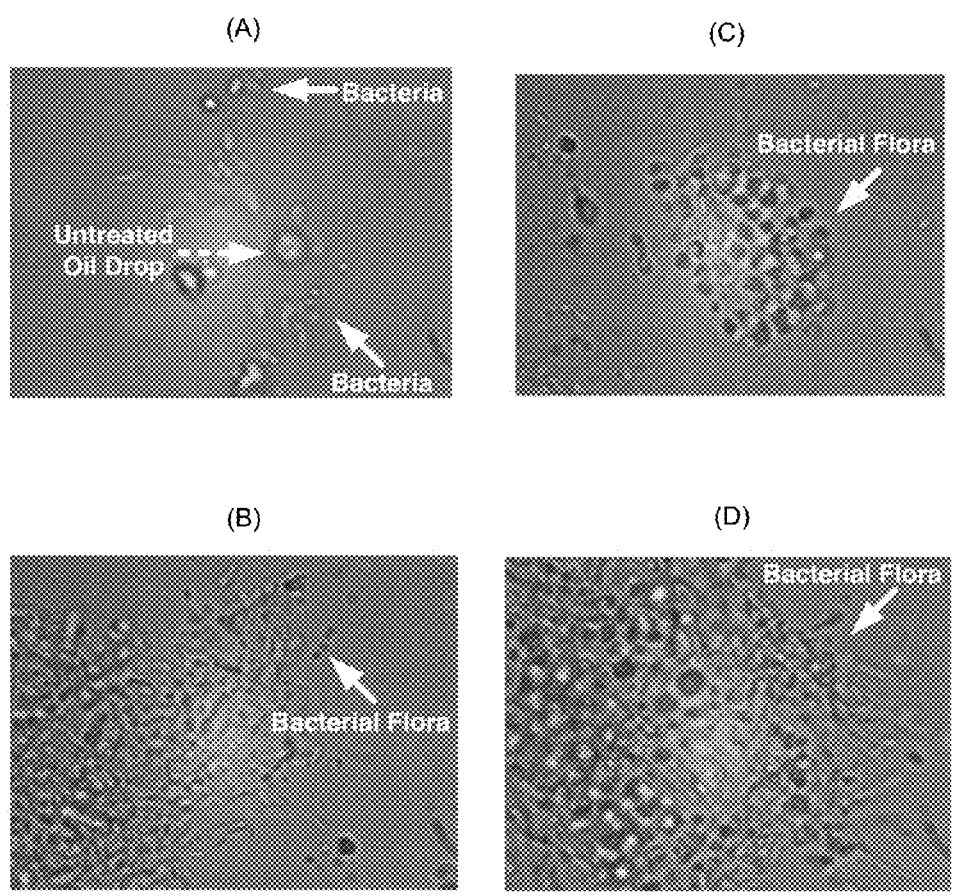
FIG. 7 includes photomicrographs (each ×1000 times) showing changes in bacteria growth in a raw-water equalizing tank. (A) shows the microbial flora state before the test start, and (B) to (D) show the states of the microbial flora after 12 days from the test start.
Figure 10:
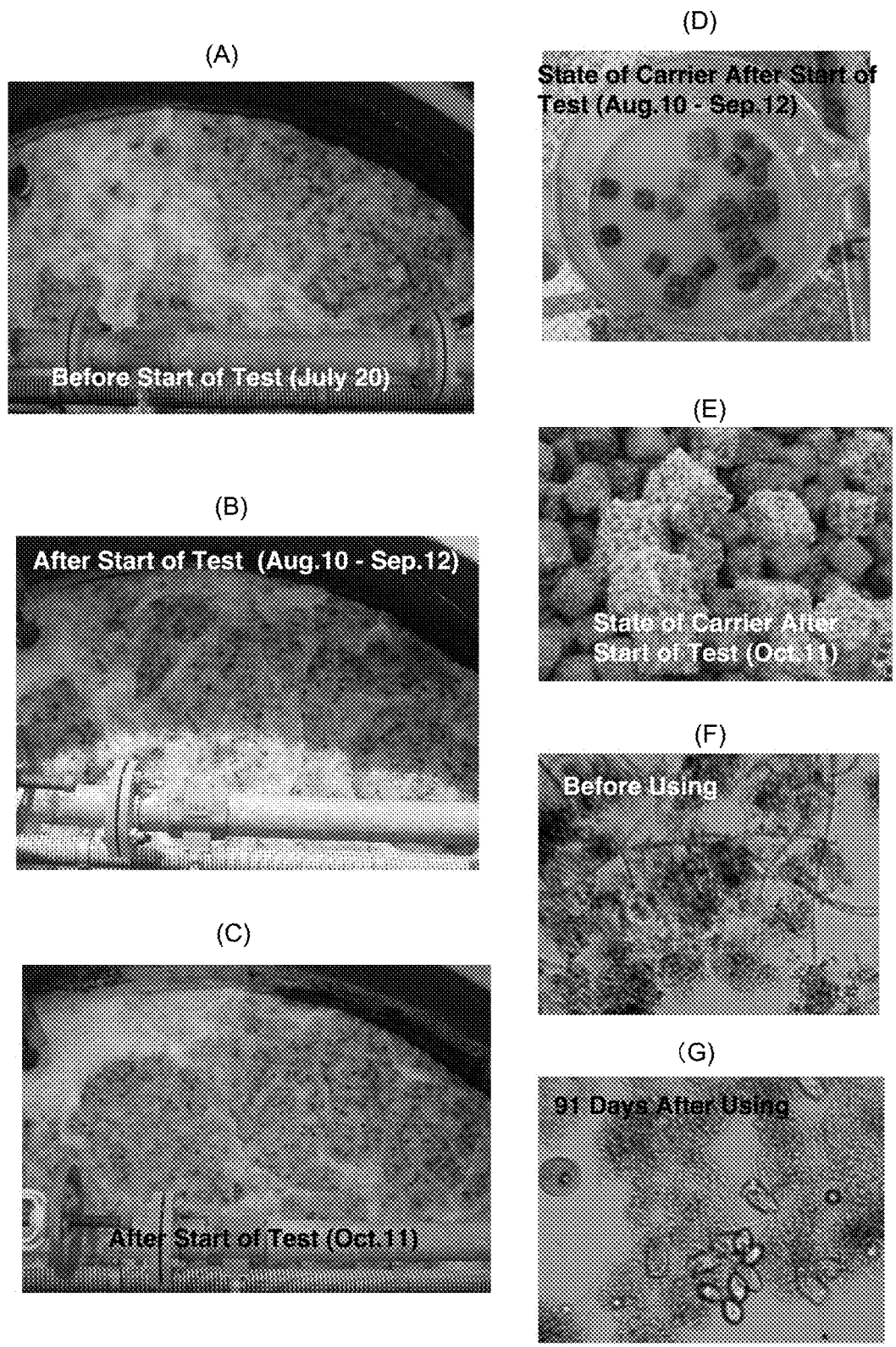
FIG. 10 includes photographs showing the changes for the state of the first carrier aeration tank before and after using the microbial flora activator of the present invention. (A) shows the state of the tank before the test start (July 20), (B) Shows the state of the tank after the test start (between August 10 to September 12), (C) shows the state of the tank after the test start (October 11). (D) This a photograph shows the state of the carrier after test start (between August 10 to September 12), and (E) Is the photograph showing the carrier after the test start (October 11). (F) is the photomicrograph showing the state of the microbial flora before using the microbial flora activator of the present invention, and (G) is a photomicrograph of the microbial flora 91 days (approximately three months) after the use of start.

Growth states of bacteria in the raw water equalizing tank are shown in FIG. 7. Untreated oil droplets and a few bacteria were observed in FIG. 7(A) which shows a state before introducing the sample 1. When 3 specimens were obtained from different locations in the same treatment tank at 12 days after addition of the sample 1, the bacteria growth and the colony formation was confirmed, but no untreated large oil droplets were observed (FIGS. 7(B) to (D)).

From the above, it was shown that the microbial flora activator of the present invention dispersed the oil and fat and the like to grow the microbes, and to decrease the sewage water load.

Example 5

Change in SS and the Like in Wastewater from the Food Factory 3

In a wastewater treatment facility (pressure floatation type) of the food factory 3, 0.0036% (v/v) of the microbial flora activator of the present invention was used to observe changes of an oil-water separation tank, the raw water equalizing tank, a stirring tank, the first carrier aeration tank, the second carrier aeration tank, and a treatment effluent tank in the states before and after the use, respectively. Among them, the tanks show the changes, the oil-water separation tank, the raw water equalizing tank, the first carrier aeration tank, and the second carrier aeration tank, are shown in FIGS. 8 to 11.

(1) Changes in the Oil-Water Separation Tank

FIGS. 8(A) to (C) show the states before and after the test start of the wastewater in the oil-water separation tank. Before the test start, oil was floating on a surface (FIG. 8(A)). After 20 days from the test start, the floating oil amount on the wastewater surface in the oil-water separation tank decreased (FIG. 8(B)). After approximately 50 days, the oil on the surface disappeared (FIG. 8(C)). Even after 80 days from the test start, no floating of oil on the wastewater surface in the oil-water separation tank was observed.

(2) Changes in the Raw Water Equalizing Tank

FIGS. 9(A) to 9(C) show the states before and after the test start of the wastewater in the raw water equalizing tank. Before the test start, brown frothy oil was floating on the surface of raw water (FIG. 9(A)). From the time of the test start, the composition of the present invention was introduced to the raw water equalizing tank with a concentration of 0.0036% (v/v). After about 20 days from the test start, the oil amount floated on the surface of the wastewater in the raw water equalizing tank decreased (FIG. 9(B)). After approximately 50 days, the oil amount floated on the surface of the wastewater still kept the decreased state, the color of the wastewater changed from a white opaque to a light gray (FIG. 9(C)).

(3) Changes in the Stirring Tank

In the stirring tank, the surface of the wastewater was covered by an oil film before the test start, and even 20 days from the test start, the existing oil film was observed. After 50 days from the test start, the oil film disappeared. After 80 days from the test start, no oil film was observed, and the color of the raw water changed from white opaque to light gray.

(4) The First Carrier Aeration Tank

FIGS. 10(A) to (C) show the states before and after the test start of the wastewater in the first carrier aeration tank. In the first aeration tank, a beige-colored porous carrier was introduced for accelerating decomposition of organic contaminants by microbes.

Before the test start, oil and the filamentous bacteria in the wastewater were adhered to the carrier. There was no environment for the aerobic microbes to grow even upon aerating (FIG. 10(A)). As 20 days passed after the test start, oil adhered to the surface of the carrier vanished, and moreover, the filamentous bacteria entangled with the carrier had almost vanished (FIG. 10(B)). During the period, white aggregated oil peeled off from the equalizing tank were also observed in the first carrier aeration tank. The carrier condition at this time is shown in FIG. 10(D).

After 80 days from the test start, the wastewater conditions in the aeration tank changed (FIG. 10(C)), and the microbes adhered to the carrier was observed (FIG. 10(E)).

The microbe conditions in the activated sludge before and after using the microbial flora activator of the present invention is shown in FIGS. 10(F) and (G). The sludge before use was poor condition for the flocculating property because of spread filamentous bacteria, and the excessive sludge generation was also large.

However, 91 days (approximately three months) after the start of use, the filamentous bacteria could hardly be observed, and the protozoa amount increased, thereby improving the flocculating property, thereby the sedimentation property of the sludge was improved significantly. The generated excessive sludge amount decreased drastically.

(5) The Second Carrier Aeration Tank

FIGS. 11(A) to (C) show the states before and after the test start of the wastewater in the second carrier aeration tank. The beige-colored porous carrier was introduced to the second carrier aeration tank for accelerating decomposition of organic contaminants by the microbes, similarly as to the first carrier aeration tank.

Before the test start, oil in the wastewater adhered to the carrier and floated on the surface of the wastewater in the water tank (FIG. 11(A)). As 50 days passed after the test start, oil adhered to the carrier vanished (FIG. 11(B)), and the wastewater also could show clearness (FIG. 11(D)). However, for the dissolved oxygen concentration (DO) in the favorable state is 2.0, it still showed a high value, 5.0.

After 80 days from the test start, the wastewater conditions in the aeration tank clearly changed (FIG. 11(C)), and the completely recovered carrier was also observed (FIG. 11(E)).

The microbe conditions in the activated sludge before and after using the microbial flora activator of the present invention is shown in FIGS. 11(F) and (G). The sludge before use was in poor condition for the flocculating property because of spread filamentous bacteria, and the excessive sludge generation was also large.

In contrast, 180 days (approximately 6 months) after the start of use, the flocculating property of the flock improved, thereby the sedimentation property improved significantly. The excessive sludge generation decreased drastically.

(6) The Treated Water Effluent Tank

In the treated water effluent tank before and after the test start, the treated water was cloudy, measured n-Hex value showed 91 mg/L. As about 50 days passed after the test start, the cloudy treated water changed to light brown color. The n-Hex value dropped down to 27 mg/L.

After 80 days from the test start, the treated water turned to clear. The n-Hex value further dropped to 12 mg/L.

Similarly as in the first carrier aeration tank, the beige-colored porous carrier was introduced for accelerating decomposition of organic contaminants by microbes.

(7) The Pipes

How an oil content adhered inside pipes changes when the pipe cleaning agent containing 1% of the microbial flora activator of the present invention was introduced to wastewater pipes was captured by a CCD camera to show in FIGS. 12(A) to (F).

FIG. 12(A) to (C) are images showing a condition inside the pipe and around an inlet of the wastewater pipe before starting the use. It showed that a thick layer of oil content is deposited thoroughly inside the pipe.

FIGS. 12(D) to (F) are images showing the condition inside the pipe and the condition around the inlet of the wastewater pipe 1 month after the start of use. A majority portion of the oil content deposited thoroughly inside the pipe has been shown to be peeled off in FIGS. 12(D) to (F).

From these observations, it was shown that the introduction of the detergent containing the microbial flora activator of the present invention inside the wastewater pipes removes the oil deposited inside the wastewater pipes.

(8) Results

Before the test start, the floating oil should be recovered every day, but after, recovering the floating oil became unnecessary. Also, because the surrounding area of the oil-water separation tank became clean, the cleaning frequency was reduced from once every week to once every six months. The oil existed in the raw water measurement tank before the test start also vanished.

Furthermore, the oil layers engrained inside the raw water equalizing tank was peeled off gradually to be sent to the treatment tank with the wastewater. By this, cleaning of inside of the wastewater equalizing tank became unnecessary. The oil layers accumulated inside the pipes was also peeled off and reduced; thereby pipe choking was resolved.

After halting the aeration tank through the weekend, a lot of foam was formed caused by the oil content in the aeration tank at the time of operating at the beginning of the subsequent week. However, the foam formation amount decreased after the test start.

From these observations, it was shown that by using the microbial flora activator of the present invention, the oil deposited in the tanks including the raw water tank, and the pipes decreased, and the wastewater was treated efficiently. This was considered due to the oil in the wastewater being dispersed; thereby the environment for the aerobic microorganisms to grow was prepared.

With progress of the oil treatment, the cost necessary for removing the oil content from the treatment tanks could be reduced drastically.

Example 6

Regarding Fluctuation in BOD and the Like in the Wastewater Treatment Facility in the Food Factory 4

In the wastewater treatment facility from the food factory 4, the microbial flora activator (stock solution) of the present invention was continuously introduced at the rate of 2.5 ml/minute for 24 hours (0.0036% of the concentration in the raw water tank), sampling was carried out periodically before and after introducing to measure the BOD, SS, and n-Hex to investigate the fluctuation over a long period.

BOD was measured according to JIS K0102 21, SS was measured according to JIS K0102 14.1, and n-Hex was measured according to appendix 4 of Environmental Agency notification No. 64.

The method for measuring n-Hex was as follows. A predetermined amount of the sample was transferred from the container including the sample to an extraction vessel. A few drops of methyl orange solution were added to the vessel as the indicator, and hydrochloric acid (1+1) was added till the color of the solution turned to red to adjust pH 4. The sample container was washed twice with 25 ml of hexane, and washings were added to the vessel to combine with the sample.

The solution in the extraction vessel was stirred for approximately 10 minutes, and then it was allowed to stand to separate a hexane layer. Next, a capillary was inserted into a bottom of the extraction vessel to transfer the almost aqueous phase to a separatory funnel. Twenty five mL of hexane was added to the vessel and shaken, thereby obtaining the washings. This operation was repeated twice. The remaining hexane phase and a small amount of water were transferred to the separatory funnel (volume 250 mL), and the washing obtained as described above was combined.

20 mL of water was added to the hexane phase to be shaken for 1 minute, and then the solution was left to separate the hexane phase and the aqueous phase. After removal of the water phase, the operation was repeated several times. Three g of anhydrous sodium sulfate was added to obtain the hexane phase to be shaken for finally remove the water content.

A filter paper was initially washed with hexane to remove the extracted materials, and then it is used to wipe a leg of the separatory funnel. Then, another filter paper similarly treated to filtrate the obtained hexane phase. The filtrates were collected in a beaker. Each filter paper used was washed twice by using 5 mL of hexane, and the washing was combined to the filtrates.

The hexane was volatilized on a hot plate heated at 80° C. Firstly, the outside of the beaker was wiped with a wet cloth, and then wiped well by using a dry cloth. Then, the beaker was transferred to an oven maintained at 80° C., and dried for 30 minutes. The beaker was moved into a desiccator to allow to cool for 30 minutes. Then, the mass was weighed up to a digit of 0.1 mg.

A similar operation was carried out by using a blank. The normal hexane extract concentration (Y) in the sample was calculated by the following equation.

$$Y(mg/L) = (a-b) \times (1{,}000/\text{sample amount}(mL))$$

In the equation, a and b are as follows.

a denotes a mass difference of the beaker wherein the sample was placed (mg) before and after the test, and b denotes the mass difference of the blank beaker (mg) of the blank before and after the test.

Figure 13:
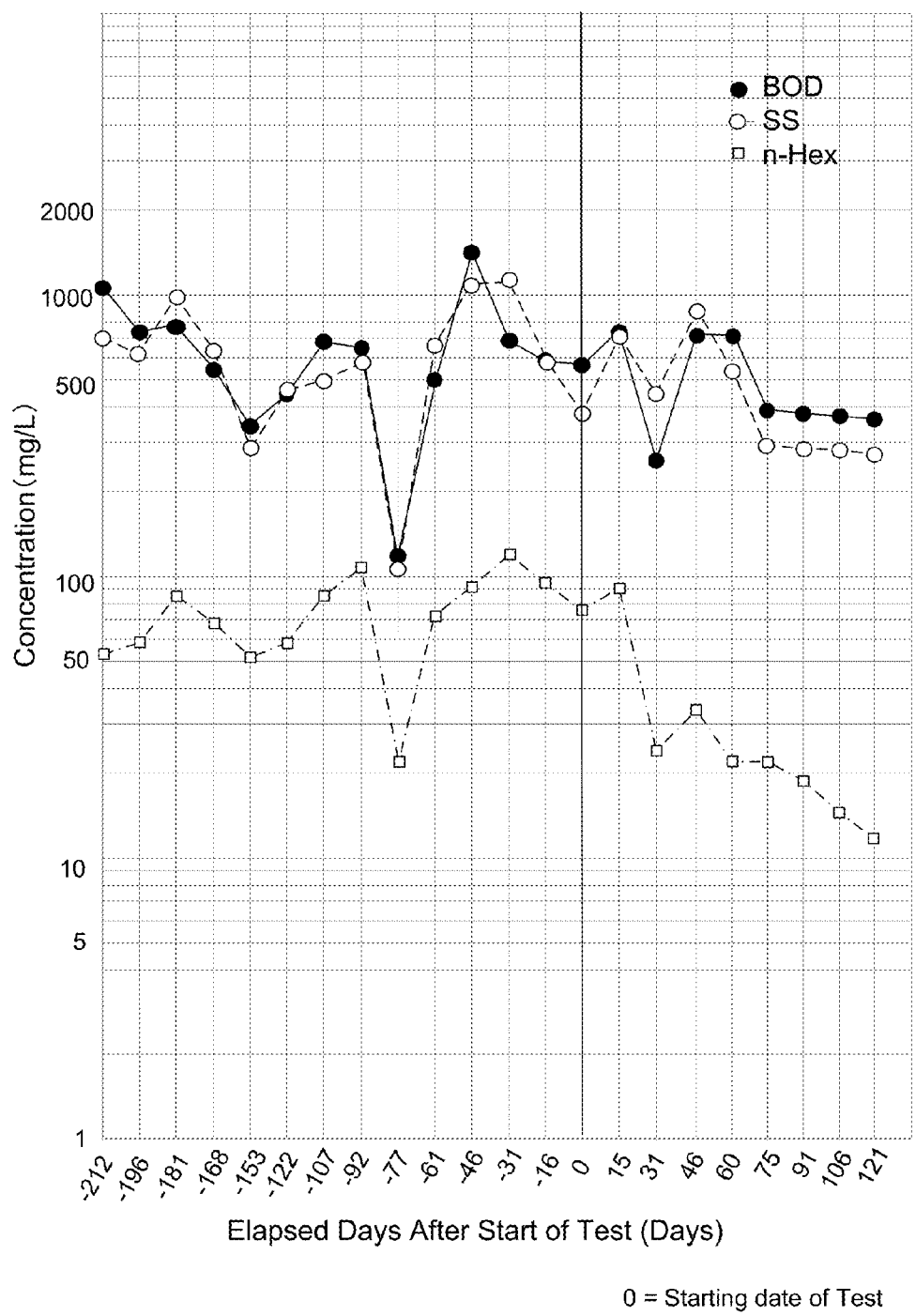
FIG. 13 is a graph showing the value fluctuations of BOD, SS, and n-Hex before and after introducing the microbial flora activator of the present invention to the raw water tank in the wastewater treatment facility of the factory.

Results are shown in the Table 5 and FIG. 13.

TABLE 5

| Date | No. of days | BOD (mg/L) | SS (mg/L) | n-Hex (mg/L) |
|---|---|---|---|---|
| Jan. 15 | −212 | 1,030 | 690 | 52 |
| Jan. 31 | −196 | 710 | 610 | 57 |
| Feb. 15 | −181 | 770 | 990 | 84 |
| Feb. 28 | −168 | 555 | 640 | 67.5 |
| Mar. 15 | −153 | 340 | 290 | 51 |
| Mar. 31 | −137 | 450 | 470 | 58 |
| Apr. 15 | −122 | 680 | 500 | 85 |
| Apr. 30 | −107 | 650 | 570 | 110 |
| May 15 | −92 | 120 | 110 | 22 |
| May 31 | −76 | 500 | 660 | 71 |
| Jun. 15 | −61 | 1,490 | 1,150 | 92 |
| Jun. 30 | −46 | 680 | 1,210 | 130 |
| Jul. 15 | −31 | 580 | 590 | 94 |
| Jul. 31 | −15 | 570 | 370 | 75 |
| Aug. 10 | 0 | 590 | 410 | 72 |
| Aug. 15 | 5 | 760 | 720 | 91 |
| Aug. 31 | 21 | 260 | 460 | 24 |
| Sep. 15 | 36 | 730 | 890 | 34 |
| Sep. 29 | 50 | 740 | 540 | 22 |
| Oct. 15 | 66 | 390 | 510 | 21 |
| Oct. 31 | 81 | 380 | — | 18 |
| Nov. 15 | 96 | 370 | — | 15 |
| Nov. 30 | 111 | 360 | — | 12 |

An average of BOD before the test start was 649.8±308.3 (mg/mL), but after the test start, it decreased about 23% to 498.7±206.6 (mg/L). SS showed decreasing tendency. n-Hex decreased approximately 60%, from 74.9±27.3 (mg/L) to 29.6±25.6 (mg/L).

After the start of adding the microbial flora activator of the present invention, both values of SS and BOD measured were increased, and then they remained at comparatively higher values for a month, and thereafter decreased. It appears that the oil content, which has been already deposited in the treatment tank and pipes before using the composition of the present invention, is gradually peeled off, and mixed into the wastewater.

Moreover, since n-Hex concentration was decreased approximately 80% after using the microbial floral activator of the present invention, it was considered that the mixed oil content was decomposed rapidly by the activated microbes.

From these observations, it was shown that the oil content in the wastewater decomposes satisfactorily to be decreased by using the composition of the present invention. Moreover, the oil content in the wastewater decomposes immediately after removably the activated microbial flora.

Example 7

Figure 14:
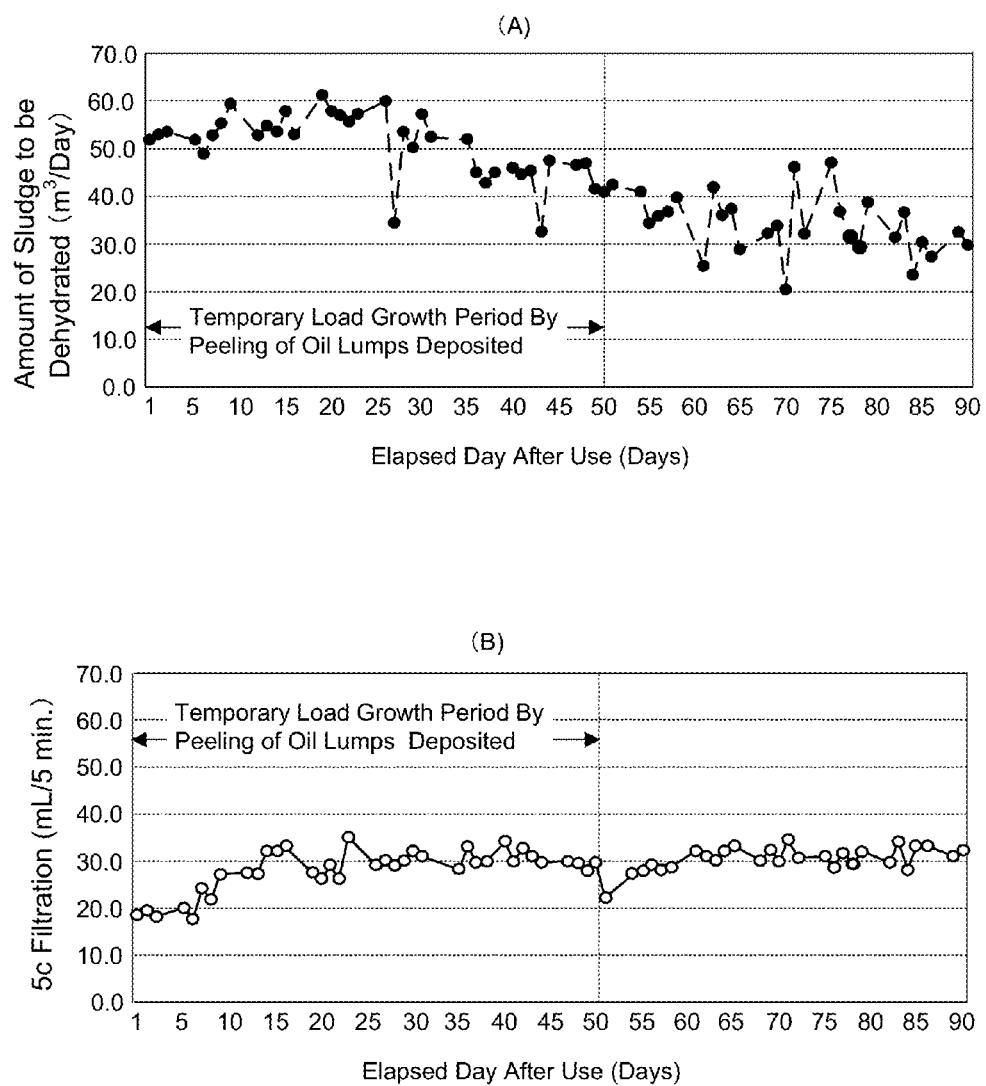
FIGS. 14 includes the diagrams showing (A) the change in a dehydrated amount from the sludge in the wastewater treatment facility of the food factory, and (B) a filtration rate of the activated sludge in the wastewater treatment facility of the food factory.
Figure 15:
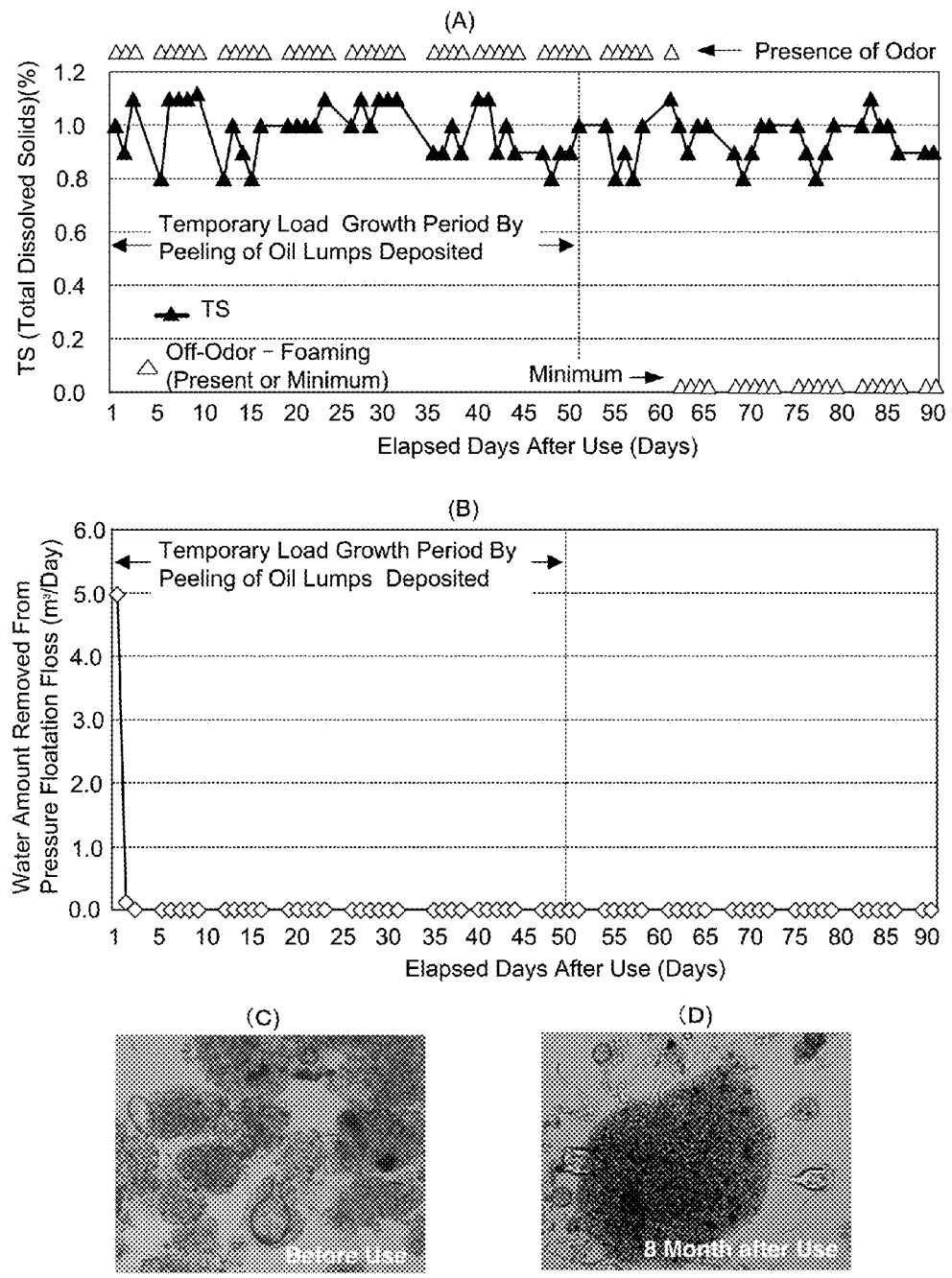
FIG. 15 includes the diagrams showing the change in total solids (TS) of the activated sludge in the membrane aeration tank of the wastewater treatment facility of the food factory, and the dehydrated amount from pressure floatation floss. (A) and (B) are graphs showing the change in the TS and the dehydrated amount from the pressure floatation floss respectively, and (C) and (D) are the photomicrographs, each showing the state of the microbial flora before and after starting the use thereof.

Regarding Change in the Dewatered Amount of the Sludge in the Wastewater Treatment Facility with an Activated-Sludge Membrane Separator The dewatered amount of sludge (m³/day) in the wastewater treatment facility of the food factory 5, a filtration rate (mL/5 min.) of the activated sludge by using No. 5C filter paper, and the total solids (%) were measured periodically to observe their fluctuations. Results are shown in FIGS. 14 and 15.

As shown in FIG. 14(A), the dewatered amount of the sludge was maintained at a high level of 50 m³/day on average for up to 35 days from the start of the use of the microbial flora activator of the present invention, but then decreased. After day 60, the dewatered amount of the sludge reduced 20 to 40% to 30 m³/day to 40 m³/day. In spite of it, the concentration of the sludge was maintained to be almost constant without rising (see FIG. 15(A)).

It was thought that the reason for being maintained higher level up to day 35 from the start of use was peeling off of the oil content deposited in the treatment tanks including the wastewater tank, and the pipes by using the microbial flora activator of the present invention.

As shown in FIG. 14(B), the filtration rate by using No. 5 filter paper (hereinafter, it is sometimes referred to as "5C filtration") was maintained at around 20 mL for several days immediately after the start of use. Then, it increased and became almost around 30 mL/5 min. By this, it was confirmed that the reasons for the membrane obstruction was reduced. Moreover, the odor also decreased significantly after 60 days from the start of the use, and there was no offensive odor sensed (see FIG. 15(A)). As shown in FIG. 15(B), the dewatered amount of the pressure floatation froth decreased dramatically immediately after the start of the use, and was almost zero thereafter.

Moreover, microbe conditions in the activated sludge after the start of use is shown in FIGS. 15(C) and (D). Before the use, the numbers of the microorganisms such as protozoa and multicellular organisms were fewer, and a solid-liquid interface of the activated sludge flock was unclear, and its flocculating property was also poor. The excessive sludge generation was extremely large.

In contrast, in the 8 months from the start of the use, the flocculating property became favorable, and the solid-liquid interface of the flock became clear. Since the sedimentation property of the activated sludge was improved, the excessive sludge generation also decreased drastically.

Example 8

Treatment of Oil and Fat in the Wastewater from the Food Factory (1) Used Processing Agents The agents shown in the Table 6 were added to the wastewater from the food factory (oil and fat content of influent water=215 mg/L). Measurement items and testing methods were as shown in the Table 7.

TABLE 6

| System | Processing agent |
|---|---|
| 1 | Nil (control) |
| 2 | Microbial flora activator of the present invention (composition of Example 7 of the present invention) |
| 3 | Noigen TDS-80 (polyoxyethylene tridecylether) ($C_{13}H_{27}O(CH_2CH_2O)_nH$) (manufactured by Daiichi Kogyo Seiyaku Co., Ltd.) |
| 4 | DAPE 0220 (EMALEX DAPE 0220 (polyoxyethylene polyoxypropylene decylether (20E.O.)) (manufactured by Nihon Emulsion Co., Ltd.) |

TABLE 7

| Measurement item | Method of measurement |
|---|---|
| Oil and fat content | n-Hex (wastewater test method) - Equivalent to JIS K0102-24 |
| T-BOD & S-BOD | General dilution method - Equivalent to JIS K0102-21 |
| T-COD & S-COD | Portable handheld water temperature measuring instrument (pHoto Flex WTW Co.) - Equivalent to JIS K0102-20 |
| SS · VSS | Glass fiber filter paper method (wastewater test method) - Equivalent to JIS K0102-14, 14.4.1 |
| MLSS · MLVSS | Centrifugal separation method (wastewater test method) - no description in JIS K0102-24 |
| Concentration of dissolved oxygen | Electrode method (wastewater test method) - Equivalent to JIS K0102-32.3 |

(2) Experimental Equipment

Figure 16:
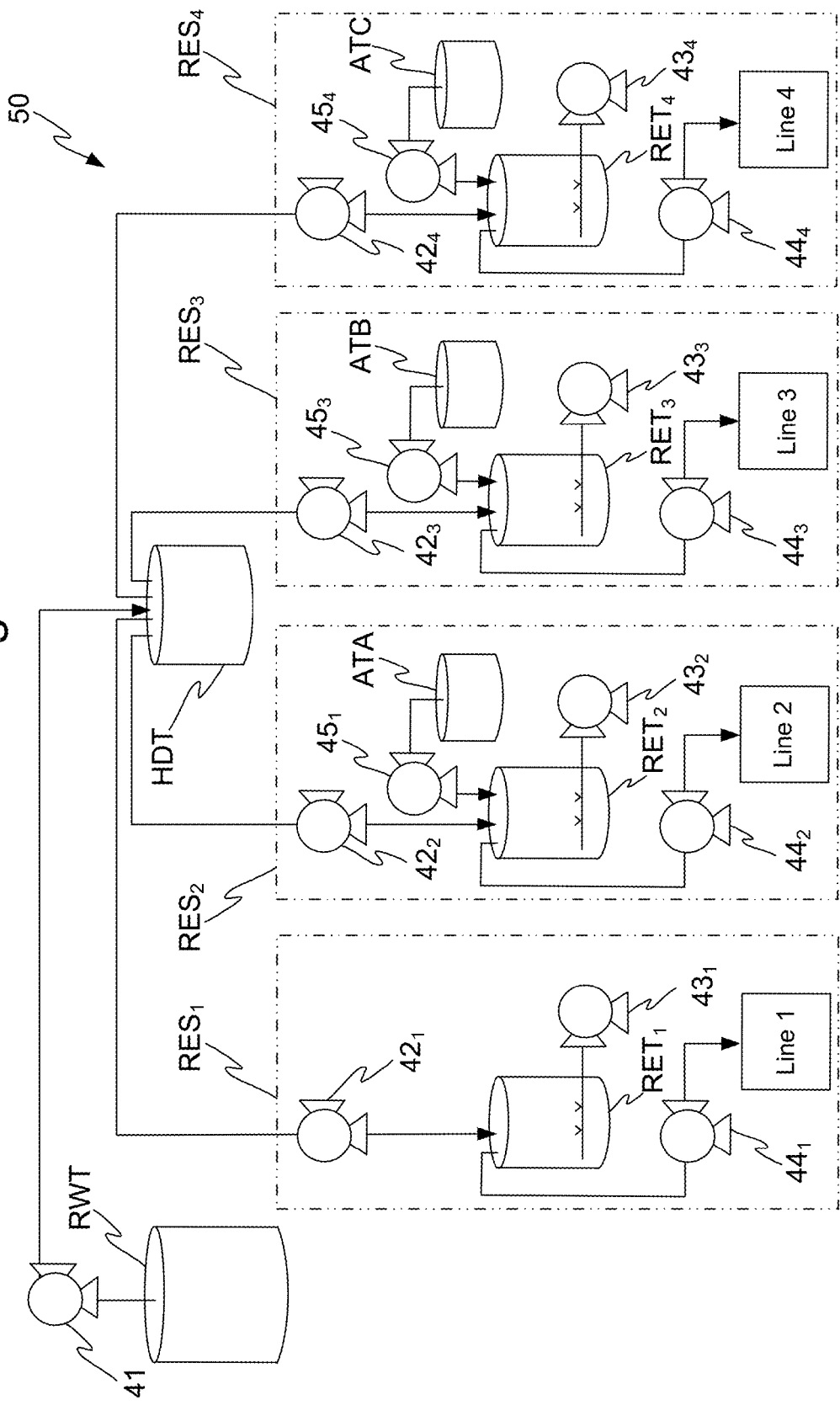
FIG. 16 is a schematic diagram of a semibatch equipment by using the activated sludge, which was used in the example.

The experimental equipment 50 used in the present examples is a semi-batch apparatus which utilizes the activated sludge. Its schematic diagram is shown in FIG. 16.

The equipment included a raw water tank RWT, a head tank HDT for supplying the raw water to each line, a reaction tank $RET_i$ (i=1 to 4) with an aerator. The raw water in the raw water tank was sent to the head tank with a pump 41, and is further supplied to each reaction tank $RET_i$ (i=1 to 4) with the pump $42_i$ (i=1 to 4). Each line was named as $RES_j$ (j=1 to 4).

The line 1 was a control line ($RES_P$) without addition of any agents. The line 2, the line 3, and the line 4 were the lines ($RES_2$, $RES_3$, and $RES_4$) to investigate effects of the agents. Each of them included the agent supply tanks ATA, ATB, and ATC respectively. Air was supplied to the reaction tank $RET_1$ by the pump $43_1$. There is a similar arrangement in other reaction tanks as well.

In the line 2, the agent A (the composition of the Example 7 of the present invention) was supplied from the agent supply tank ATA to the reaction tank with the pump 45. In the line 3, the agent B (TDS-80) was supplied to the reaction tank, and in the line 4, the agent C (DAPE-0220) was supplied to the reaction tank.

In order to prevent aggregation of the solid content, and oil and fat, the raw water tank RWT was kept at 35° C. while stirring. Also, a height of the head tank HDT was fixed, and an arrangement was made to supply a uniform amount of wastewater all the time to each line, without depending on a water level in the raw water tank RWT.

The raw water and the respective processing agents were added to the reaction tanks $RET_1$, $RET_2$, $RET_S$, and $RET_4$. By the time point of 12 weeks from the test start, the sludge was aerated for 6 hours and then allowed to the sedimentation separation for 2 hours. Then, 3,000 mL of the supernatant was extracted by using the pump $44_i$ (i=1 to 4). The introduction amount of the surfactant during this period was 0.33 mg/L as the concentration diluted by using the raw water in each line. No surfactant was added to the line 1, the control line.

From 12 weeks to 19 weeks from the test start, the sludge was aerated for 6 hours and then allowed to the sedimentation separation for 2 hours. Then, 2,000 mL of the supernatant was extracted by using the pump $44_i$ (i=1 to 4). The introduction amount of the surfactant during this period was 0.33 mg/L as the concentration diluted by using the raw water in each line. No surfactant was added to the line 1, the control line.

After 19 weeks from the test start, the sludge was aerated for 6 hours and then allowed to the sedimentation separation for 2 hours. Then, 2,000 mL of the supernatant was extracted by using the pump $44_i$ (i=1 to 4).

The introduction amount of the surfactant during this period was 0.33 mg/L as the concentration diluted by using the raw water in each line. No surfactant was added to the line 1, the control line. The introduction amount of the surfactant during this period was 1.0 mg/L as the concentration diluted by using the raw water in each line. No surfactant was added to the line 1, the control line. An effective volume of the reaction tank in the experiment was 6 L. Measurement results are shown in the Table 8.

TABLE 8

| Measurement | Measurement results | | | |
|---|---|---|---|---|
| items | Control | Line 2 | Line 3 | Line 4 |
| S-BOD (mg/L) | 49 (100.0) | 53 (108.2) | 43 (87.7) | 59 (120.4) |
| n-Hex (mg/L) | 17.9 (100.0) | 14.4 (80.4) | 28.3 (158.1) | 12.9 (72.1) |
| Oil and fat content in sludge (mg/g) | 23.4 (100.0) | 10.6 (45.3) | 13.0 (55.4) | 22.4 (95.7) |
| Amount of sludge generated (g/day) | 1.49 (100.0) | 1.27 (85.2) | 1.46 (98.0) | 1.51 (101.3) |

As shown in FIG. 8, in the line 3, the result showed that n-Hex concentration was high, and the oil and fat content in the sludge was low. This means that oil and fat in the wastewater was dispersed, and were only adhered not but incorporated in the sludge sufficiently; and the dispersed oil and fat was not decomposed. Alternatively, in the line 4, the n-Hex concentration in the wastewater was low, but the content in the sludge was large. It was shown that almost all of the oil and fat adhered to the sludge, but was not decomposed by the microbes. This was also supported by a fact that the line 4 had granular type sludge. By this, it was shown that problems for weakening the decomposition capability of organic contaminants other than oil and fat, and increasing the sludge generation were caused, when the sludge is actively extracted to remove oil and fat.

In contrast, in the line 2, both of the n-Hex concentration and oil and fat content in the activated sludge were low, and the sludge generation was decreased. Therefore, in the line 2, it was shown that the oil and fat content in the wastewater was well dispersed, and the dispersed oil and fat were not simply adsorbed in the sludge, but decomposed by the microbes. Nevertheless, the growth of the microbes was not observed.

Furthermore, the sludge generation (per day) in the line 2 was less by approximately 15% as compared with that of the control. This is the effect derived from the decomposition by the microbes as described above, and it enables to reduce the extraction amount of the sludge. Then, since the treatment efficiency may be kept high, it leads to reduce the cost for treating the excess sludge.

(3) Variation Per Day of SVI in the Treated Water

Figure 17:
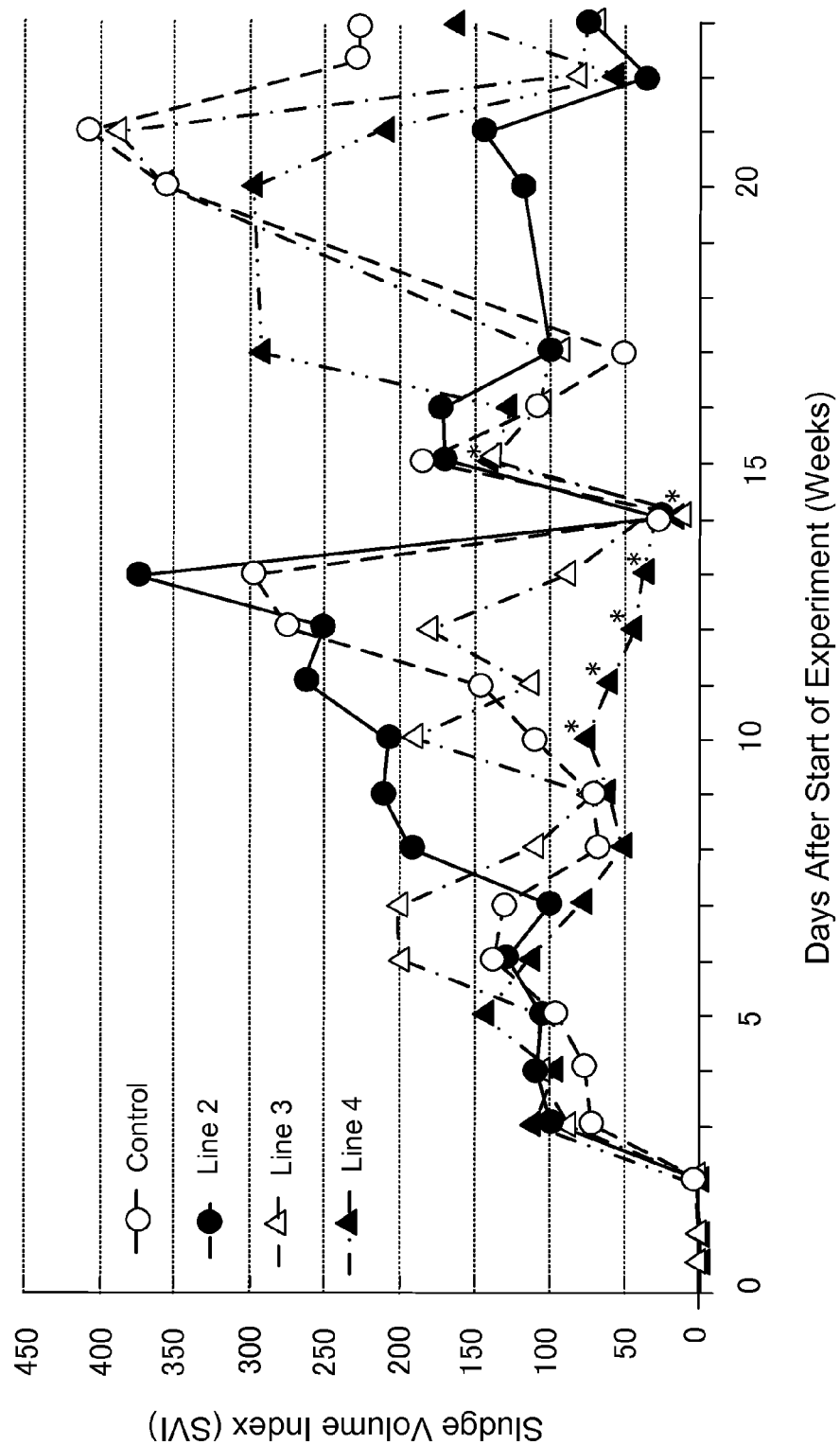
FIG. 17 is a graph showing results of a study of the fluctuations for the SVI of the water treated by the equipment, by using the wastewater from the food factory.

Variation of the sludge volume index (SVI) depending on the types and the added amounts was investigated. The results are shown in FIG. 17.

The sludge volume index (SVI) was calculated by the following equation (I).

$$SVI = SV \times 10,000 / MLSS \qquad (I)$$

In the equation, SV denotes a sedimentation ratio of the activated sludge, and MLSS denotes a suspended solid (SS) in the mixed solution. It refers to suspended substances of the activated sludge (mg/L) in the aeration tank. The SVI shows a volume occupied by 1 g of sludge indicated as mL, a high SVI value means that the activated sludge has poor flocculation and sedimentation properties.

Figure 18:
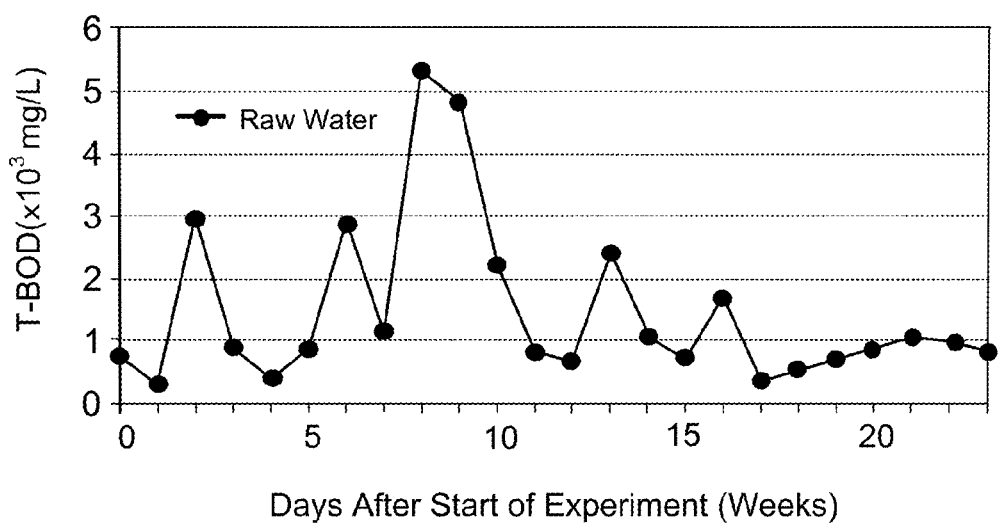
FIG. 18 is a graph showing the result when the change in T-BOD of the raw water (factory wastewater) after starting the test was measured by using JIS K0102 21.

Retention time of the raw water in the reaction tank throughout the period of the test was about 24 hours. As shown in FIG. 18, from the test start to the 19 weeks, the wastewater concentration from the food factory, the raw water, was entirely high, and the concentration varied largely. The maximum BOD volume load during the period reached 5.85 kg/m$^3$/day, which is more than 7 times of that written in the sewer design guidelines.

On the other hand, after 19 weeks, the wastewater concentration from the food factory was entirely low, and the concentration varied littlel. The maximum BOD volume load during the period was 1.42 kg/m$^3$/day, which is less than twice that described in the sewer design guidelines.

As shown in FIG. 17, all the lines except the line 4 indicated a high SVI value during a period from the 7 weeks to the 13 weeks. As mentioned above, this was considered that the concentration of the raw water varied largely, accompanying with the continuous transition of the biota corresponding to the variation. Only the line 4 demonstrated a small SVI value during this period. This is caused by the granular type of sludge in the line 4 with a diameter in a range of 0.5 to 1 mm. As shown in FIG. 8, since the oil and fat content in the sludge in the line 4 is large, it was considered that a biological treatment did not progressed in the line 4.

On the other hand, after the 19 weeks, the SVI value of the line 2 was low, in a range of 50 to 150, and the sedimentation property of the sludge was maintained. In contrast, the SVI values in other lines were high to show that the sedimentation properties of the sludge became worse. The reason was considered that the influent concentration was comparatively lower, and varied also small, and an increase of the introduction concentration of the surfactant for the stage at which influent was diluted with the raw water up to 1.0 mg/L gives such effects.

From these observations, in a range of an appropriate BOD load, it was shown that the introduction of the surfactant of the present invention with an appropriate concentration gives improved effect in the sedimentation property of the sludge.

Example 9

Investigation of Treatment Efficiency of the Wastewater Containing Oil

When variation in the BOD of the raw water (factory wastewater) after the test start was investigated by measuring it according to JIS K0102 21, it showed results as shown in FIG. 18. It showed that the variation width became more than 10 times large. To eliminate an effect from such variation in BOD, artificial wastewater was prepared to carry out the experiment, in the following example.

(1) Preparation of Artificial Wastewater and Treatment Agents Used

The composition of the artificial wastewater was shown as in Table 9 (the amount against 1000 mL of water). Four lines as shown in the Table 8 were prepared, and treatment efficiency of the wastewater was investigated.

TABLE 9

| Composition | Conc. (g/L) |
| --- | --- |
| Glucose | 0.56 |
| Polypeptone | 1.68 |
| Sodium hydrogen carbonate | 0.60 |
| Potassium dihydrogen phosphate | 0.10 |
| Sodium chloride | 0.40 |
| Ammonium chloride | 0.40 |
| Kaolin | 0.012 |
| Calcium chloride | 0.004 |
| GT influent water | 80 mL/L |
| Oil and fat (rapeseed oil) | 1.0 |
| Processing agent | $3.3 \times 10^{-3}$ |

Figure 19:
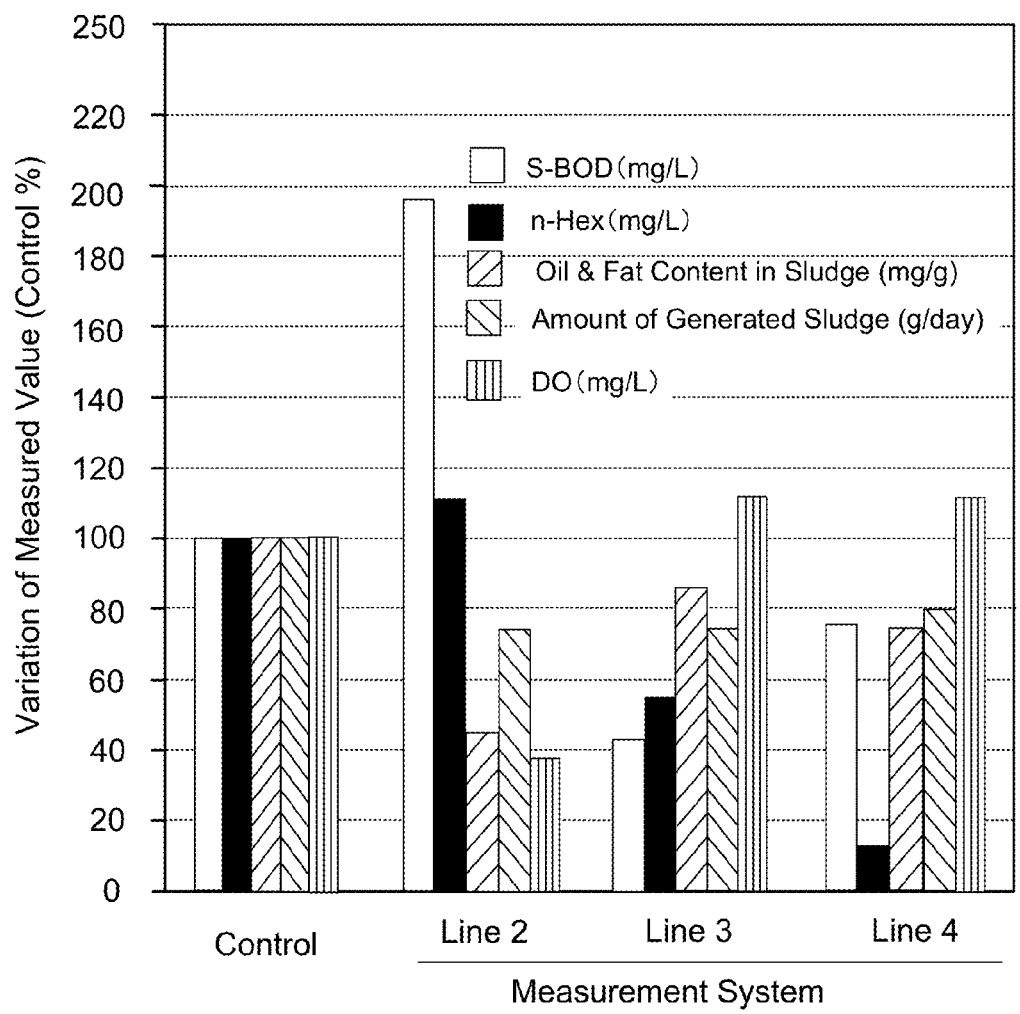
FIG. 19 is a graph showing the comparison in the respective system of S-BOD, n-Hex, oil and fat content in the sludge, the amount of the generated sludge, and DO, when artificial wastewater (oil and fat content=1007 mg/L) including GT influent water was used.

(2) Treatment Action on Oil and Fat in the Artificial Wastewater Containing GT (A Grease-Trap of an Outlet of the University Canteen) Influent Water Treatment was performed according to the above-mentioned conditions, by using the artificial wastewater containing GT influent water (the oil and fat content of GT influent water=7 mg/L, actual concentration of oil and fat content in the influent water was 1,007 mg/L, because it contains rapeseed oil). The following items were measured. Measurement results are shown in the Table 10 and FIG. 19.

Properties of wastewater, which was the mixture of the waste water and activated sludge, in each system on the 10th day from the test start were observed macroscopically to investigate which types of sludge (scum) were generated. Results are shown in FIG. 20. In the lines other than the line 2, to which the microbial flora activator of the present invention was added, scums with high oil content percentage were generated. This indicated that the oil in the wastewater was not decomposed and floated on the surface of the wastewater by separation. By this, it clearly showed that the scum treatment needed costs.

Here, S-BOD is an abbreviation of soluble BOD, and refers to BOD measured after filtration by a filter with a pore size of 1 μm, namely, refers to BOD without the solids.

In the artificial wastewater with high oil content, the line 3 and the line 4 showed high fat and oil content amount. However, S-BOD concentration was low, and the dissolved oxygen concentration was high. This implies that the microbes could not work sufficiently, because of the presence of the oil and fat content. By this, it was shown that the microbial flora incorporated oil and fat, but not decomposed them. Moreover, the sludge generation in the line 4 was increased.

In contrast, the line 2 showed both of low oil content percentage and the dissolved oxygen concentration in the sludge. The low oil content percentage in the sludge implies that the oil is well dispersed, and decomposed rapidly by the microbes in the sludge. Also, the low dissolved oxygen concentration implies that the microbes were active and work. The sludge generation was small.

Both of S-BOD and n-Hex became high, which means that the oil content amount is well dispersed, and it is decomposed by the microbes quickly. This also indicates that the activated microbes decomposed organic substances other than the oil content amount rapidly. It was considered that the microbe incorporated the oil content amount, but still remained excess oil content, and it gives high S-BOD, and as a result, the oil dispersion and the treatment of the oil by the microbes are not balanced.

As mentioned above, data showing that both of the oil content percentage in the activated sludge and the sludge generation decrease, and the dissolved oxygen concentration becomes low, when the microbial flora activator of the present invention is added was obtained. By this, it was shown that the microbial flora activator of the present invention disperse the oil in the wastewater to the appropriate size for the microbes to utilize them.

Example 10

Cleaning Test of Contamination Sample (1) Materials and Methods

A skinless fillet, which is cut opened and dried fish, was scratched by using a small blade to prepare contamination sample.

The contamination sample was rubbed sufficiently on a cutting board damaged with a kitchen knife. Then, the contaminants were wiped off by using a paper towel till the contamination became invisible. The cutting board was dried for 3 minutes to prepare a sample before cleaning.

Next, the cutting board with the contamination sample rubbed thereon was washed well with a brush by using commercially available chlorine-based alkaline detergent, a detergent containing 0.01% of the composition of the sample 1, or

TABLE 10

| Measurement items | Measurement results | | | |
| --- | --- | --- | --- | --- |
| | Control | Line 2 | Line 3 | Line 4 |
| S-BOD (mg/L) | 48 (100.0) | 94 (195.8) | 21 (43.7) | 37 (77.1) |
| n-Hex (mg/L) | 153 (100.0) | 173 (113.1) | 86 (56.2) | 20 (13.1) |
| Oil and fat in sludge (mg/g) | 17.5 (100.0) | 8.0 (45.7) | 15.4 (88.0) | 13.2 (75.4) |
| Sludge generation (g/day) | 1.27 (100.0) | 0.97 (76.3) | 0.97 (76.3) | 1.03 (81.1) |
| Dissolved oxygen conc. (mg-O/L) | 4.17-8.24 (100.0) | 0.50-4.22 (38.0) | 5.52-8.44 (112.4) | 5.40-8.40) (111.1 | a detergent containing 0.01%, all of them are used in an equal amount. Then, it was rinsed with running water until the detergents or the composition 7 of the present invention was washed out completely. The cutting board was allowed to stand for 3 minutes to prepare a sample after cleaning.

All of the samples we subjected to swab test by using Lumitester (manufactured by Kikkoman Corporation).

(2) Results

Results are shown in the Table 11. A reduction rate of the contamination after the washing was 82.5% in a case of water, when that before washing is 100. In contrast, that of the chlorine-based alkaline detergent was 95.4%.

The microbial flora activator of the present invention showed that it washed away the contaminant more than use of the chlorine-base alkaline detergent. The reduction rate was 98.0%, when it was used at the concentration of 1%, and 97.5%, when it was used at the concentration of 0.1%. Between them, there was almost no difference.

TABLE 11

| | | Type of detergent | | |
|---|---|---|---|---|
| | | Chlorine-based | Microbial flora activator | |
| | Water | alkaline detergent | 0.1% | 0.01% |
| Before washing | 80,470 (100) | 39,843 (100) | 80,470 (100) | 42,171 (100) |
| After washing | 14,126 (17.5) | 2,640 (6.63) | 1,587 (1.97) | 1,064 (2.52) |
| Reduction rate (%) | 82.5 | 95.4 | 98.0 | 97.5 |

From the above, it was shown that the composition of the present invention has stronger detergency than those of the chlorine-based alkaline detergent. When compared with the remained contamination amount, the microbial flora activator of the present invention showed twice or three times stronger detergency than that of the chlorine-base alkaline detergent.

From these observations, it was shown that the composition of the present invention has higher dispersion properties for the oil and grease contamination.

Example 11

Cleanup of the Wastewater in the Food Factory 3

To start with, 0.0006% of the microbial flora activator of the present invention was added to the raw water equalizing tank, and 1 L of the wastewater allowed passing through the floatation equipment without adding the flocculating agent was collected similarly as those in the Example 3. Items shown in the Table 12 were measured according to JIS-K0102. The retention time of the contaminated water in the raw water equalizing tank was set to 24 hours, and the DO and the MLSS in the aeration tank were in a range of 1 mg/L to 3 mg/L and a range of 5,500 mg/L and 6,500 mg/L, respectively.

TABLE 12

| | | Sampling day | |
|---|---|---|---|
| Measurement items | | April average | Jun. & Jul. average |
| Raw water (PM) (COD (mg/L)) | Before pressure | 94.5 (100.0) | 66.0 (69.8) |
| | After pressure | 31.6 (100.0) | 31.7 (100.3) |

TABLE 12-continued

| | Sampling day | |
|---|---|---|
| Measurement items | April average | Jun. & Jul. average |
| Effluent (PM) (COD (mg/L)) | 2.7 (100.0) | 2.8 (103.7) |
| PAC (L/month) | 5215 (100.0) | 2290 (43.9) |
| Anion (kg/month) | 61.62 (100.0) | 37.08 (60.1) |
| Cation (kg/month) | 125.52 (100.0) | 75.34 (60.0) |
| NaOH (L/month) | 770.0 (100.0) | 510.0 (66.2) |
| Sludge weight (kg/month) | 51847 (100.0) | 37812 (72.9) |

As shown in the Table 12, COD flowing into the floatation equipment after the use decreased as compared to that into the floatation equipment before use. This showed that the load was decreased in the wastewater equalizing tank.

Moreover, after passing through the floatation unit, the COD hardly changed. This showed that load removal efficiency in the floatation equipment was decreased. The reason was from the passing through of the refined oil and fat and the like. It was supported by the drastic reduction of the used amounts of PAC, anions, and cations.

On the other hand, according to COD (mg/L) of the effluent, the average in April was 3.4, that in June and July were 3.1. For BOD (mg/L), the average in April was 3.1, and that in June and July was 2.3. For n-Hex (mg/L), the average in April was 1.8, and that in June and July was 1.4. Therefore, almost no change observed in the quality of water. Furthermore, large number of protozoa was grown in the aeration tank, and the sludge generation drastically decreased due to the endogenous respiration. Consequently, it showed the drastic reduction of the cost for the wastewater treatment.

From these observations, it was shown that the microbial flora activator of the present invention has an excellent effect for activating the microbial floras.

Example 12

Effect of Microbial Flora Activator on Membrane Separator Type Activated Sludge Treatment Equipment An effect of the microbial flora activator of the present invention on the wastewater treatment was examined by using the membrane separator type activated sludge treatment equipment.

(1) Equipment and the Like

Figure 21:
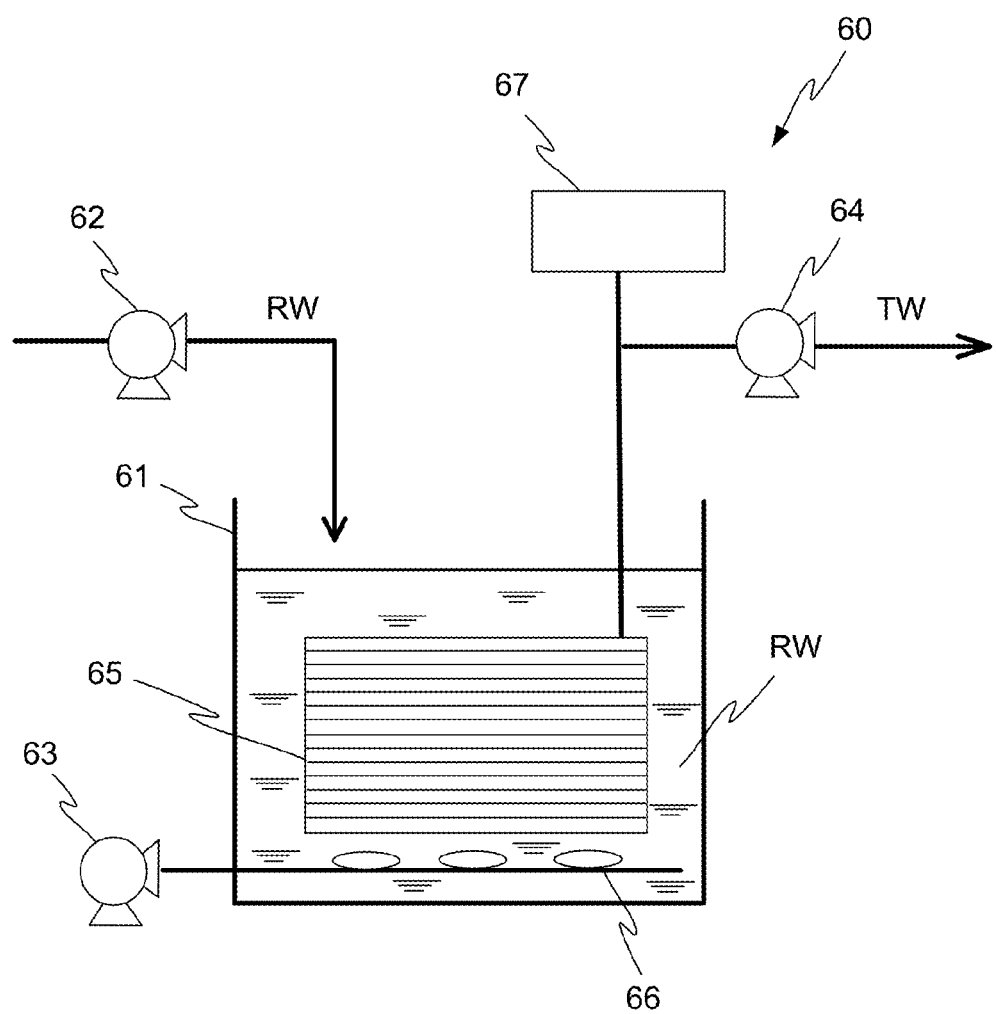
FIG. 21 is a schematic diagram of the apparatus used to study effects of the microbial flora activator of the present invention against the membrane separation activated sludge equipment.

Two lines of membrane separation type activated sludge equipment 60 (reaction tank capacity=4.5 L), which has a structure as shown in FIG. 21, were prepared. A membrane of the membrane unit 65 used here has hollow fibers made of PVDF. A pressure gauge 67 was used that pointing 0 under the atmospheric pressure. By this, since minus values of suction pressures by pumps 62 and 64 were indicated, an absolute scale leading of the pressure gauge 67 were set to the transmembrane pressure differences.

In order to oxygen supply to the reaction tank 61 and the surface washing of the membrane, aeration was performed by using the pump 63 via the diffuser 66 from directly under the membrane. A blowing amount of air was 5 L/min respectively.

No agent was charged into the control, and the microbial flora agent of the present invention was charged at 3.3 mg/L into the example. The water temperature in the reaction tank 61 was in a range of 20° C. to 23° C.

(2) Activated Sludge and the Like

The activated sludge obtained from the wastewater treatment facility of the food factory was conditioned for approximately 1 month by using artificial wastewater, of which composition was shown in the Table 13. This was used as seed sludge (the activated sludge to be introduced to the raw water in the beginning is referred to as "seed sludge"). The artificial wastewater including 0.5 g rapeseed oil per 1 L of the raw water was used for the test.

The oil and fat concentration of the artificial wastewater was 507 mg/L, which was sum of added amount 500 mg/L, and that originally included in the artificial wastewater, 7 mg/L.

TABLE 13

| Reagent | Concentration (g/L) |
| --- | --- |
| Glucose | 0.56 |
| Polypeptone | 1.68 |
| Sodium hydrogen carbonate | 0.6 |
| Potassium dihydrogen phosphate | 0.1 |
| Sodium chloride | 0.4 |
| Ammonium chloride | 0.228 |
| Kaolin | 0.012 |
| Calcium chloride (dihydrate) | 0.004 |
| GT influent water (mL/L) | 80 |

* Grease-trap influent for University canteen wastewater treatment (3) Test Method Firstly, pure water was run through the equipment to confirm that a relationship between a pressure and a permeation flow rate was equivalent, and that the equipment performances of the two lines were equivalent.

Next, the 4.5 L of the seed sludge prepared as described above was charged into the reaction tank 61. The equipment was started by using the cycle repeating such as the raw water charge—24 hour aeration—30 minutes extraction of the treated water. The extracting and charging amounts per time of the artificial wastewater were 1.5 L respectively.

The treatment water amount (the transmembrane water amount) and pressure were measured 10 minutes after the extraction start. For the pressure, a value of the pressure gauge 67 at the location shown in FIG. 21 was read, and the transmembrane pressure difference was calculated. The outside pressure to the membrane was the atmospheric pressure+ depth pressure. Since a membrane depth was shallow, it is almost same as the atmospheric pressure. Therefore, the value read on the pressure gauge was recorded as is. BOD was measured according to the general dilution method (sewage test method).

Figure 22:
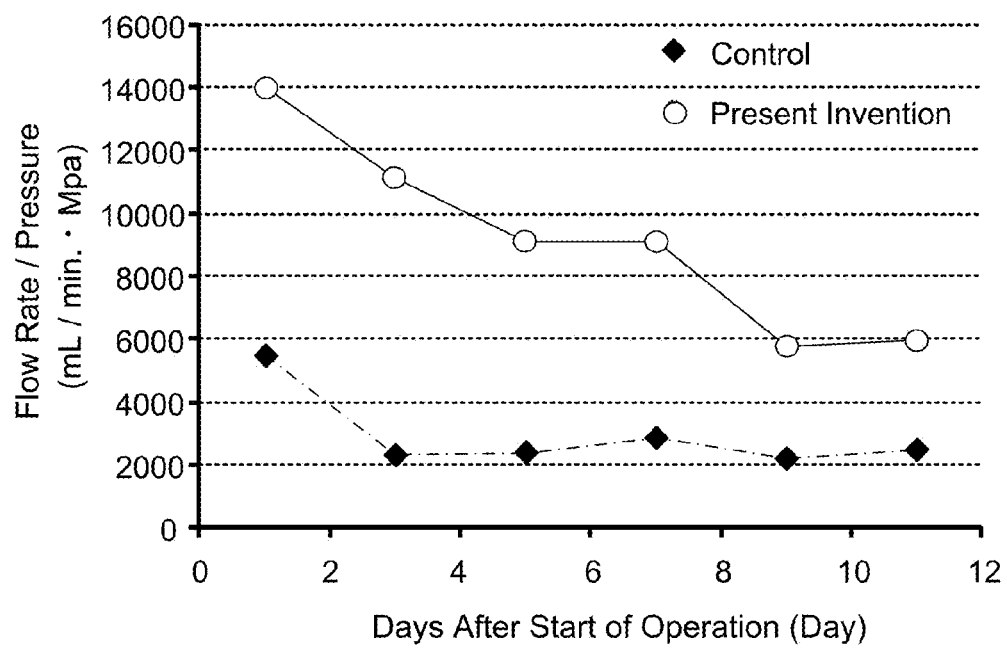
FIG. 22 is a graph showing the change in a permeation flow rate / transmembrane pressure difference with the elapsed days after the operation start.

Results are shown in FIG. 22. In FIG. 22, the horizontal axis represents the elapsed days, and a vertical axis represents the value obtained by dividing a permeation flow rate with the transmembrane pressure difference.

In the present example, the ratio of the flow rate/pressure was 2 to 4 times that of the control line, and it showed the effect of addition of the microbial flora activator of the present invention. After the test termination, the membrane units used as the control or the sample was pulled out from the respective reaction tank to be observed the condition thereof. The result was shown in FIG. 23. There was a large difference in the amount of the sludge containing oil adhered to the membrane unit 65 used in the control, and that used in the present example, and the membrane unit 65 used as the present example was far small.

From the above, it was shown that the use of the microbial flora activator of the present invention gave the high permeation velocity/pressure with low pressure. As demonstrated in the Examples 1 to 11, this because the sludge is not sticky, since the decomposition of the oil content in the wastewater is performed rapidly.

In such manner, due to achieve a high permeation flow rate/transmembrane pressure difference, it enables not only the reduction of an energy for operating the suction pump, which dominates a major part of a consumption energy of the membrane separating activate sludge, but also the achievement of an equal amount of treated water by using a small-size equipment. In other words, there is no need to build a large-size facility, and there are many advantages from a viewpoint of construction of the facility.

In the membrane separation equipment, in addition to the membrane surface washing by using the general aeration, a periodical cleaning with removal of the membrane unit and with the cleaning agent are necessary. However, when the high permeation flow rate / transmembrane pressure difference is achieved, it is possible to reduce a cleaning cost, because it is possible to elongate the cycle of these periodical cleanings (by reducing the frequency of cleaning).

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of em bodiments of the invention that are described, and embodiments of the invention comprising different combinations of features noted in the described embodimen ts, will occur to persons of the art. The scope of the invention is limited only by the claims.

Various references are cited throughout this specification, each of which is incorporated herein by reference in its entirety.

What is claimed is:

1. A microbial flora activator comprising:
    0.0005 to 8 wt % of polyoxyalkylene alkylether having a branched carbon number in a range of 13 to 22, to which ethylene oxide is added at molar number either between 8 and 10 or between 16 and 20, and 0.0005 to 2 wt % of fatty acid dialkanolamide as main components;
    and water as a remainder.

2. The microbial flora activator according to claim 1, wherein the polyoxyalkylene alkylether is a compound selected from the group consisting of polyoxyalkylene tridecylether, polyoxyalkylene tetradecylether, polyoxyalkylene pentadecylether, polyoxyalkylene isocetyldecylether, polyoxyalkylene hexyldecylether, polyoxyalkylene heptyldecylether, polyoxyalkylene octyldecylether, polyoxyalkylene octyldodecylether, polyoxyalkylene nonyldecylether, polyoxyalkylene decyldecylether, polyoxyalkylene undecyldecylether, and polyoxyalkylene behenylether.

3. The microbial flora activator according to claim 1, wherein the polyoxyalkylene alkylether is the compound selected from the group consisting of polyoxyethylene ethers and polyoxypropylene ethers.

4. The microbial flora activator according to claim 1, wherein the fatty acid dialkanolamide is the compound selected from the group consisting of coconut-oil fatty acid diethanolamide and coconut-oil fatty acid dipropanolamide.

5. An anti-filamentous bacteria agent having the microbial flora activator according to claim 1 as an active ingredient.

6. A pipe cleaning agent having the microbial flora activator according to claim 1 as an active ingredient.

7. A method for treating wastewater containing oil and fat and the like comprising the steps of:
   (a) introducing the microbial flora activator according to claim 1, to raw water;
   (b) eliminating dispersed oil and fat in the raw water by using the microbial flora activator along with other organic contaminants to process; and
   (c) gravity separating the activated sludge stably by improving sedimentation property of activated sludge in an aeration tank without a flocculate coagulator, or separating with a membrane.

8. The method for treating wastewater containing oil and fat and the like according to claim 7, wherein in the introducing step, the microbial flora activator is introduced to the raw water stored in the raw water tank or a raw-water equalizing tank, and then stirred.

9. The method for treating wastewater containing oil and fat and the like according to claim 7, wherein an amount of the microbial flora activator to be introduced in the introducing step is in a range of 0.0003 to 0.02% (v/v) against a volume of the wastewater containing oil and fat and the like in the raw water tank or the raw-water equalizing tank.

10. The method for treating wastewater containing oil and fat and the like according to claim 7, wherein a concentration of dissolved oxygen in effluent in the aeration tank is in the range of 0.1 mg/L to 5 mg/L, and that of a suspended solid (MLSS) is in the range of 4,000 to 10,000 mg/L.

11. The method for treating wastewater containing oil and fat and the like according to claim 7, wherein a membrane unit for separating activated sludge is employed in the step for separating with the membrane.

12. The method for treating wastewater containing oil and fat and the like according to claim 11, wherein the membrane unit is composed of a hollow fiber.

\* \* \* \* \*